(12) United States Patent
Noteborn et al.

(10) Patent No.: US 6,472,142 B1
(45) Date of Patent: Oct. 29, 2002

(54) METHODS AND MEANS FOR INDUCING APOPTOSIS BY INTERFERING WITH BIP-LIKE PROTEINS

(75) Inventors: Mathieu Hubertus Maria Noteborn, Leiderdorp; Astrid Adriana Anna Maria Danen-Van Oorschot, Berkel en Rodenrijs, both of (NL)

(73) Assignee: Leadd B.V., Leiden (NL)

( * ) Notice: Subject to any disclaimer, the term of this patent is extended or adjusted under 35 U.S.C. 154(b) by 0 days.

(21) Appl. No.: 09/581,001

(22) PCT Filed: Dec. 3, 1998

(86) PCT No.: PCT/NL98/00688

§ 371 (c)(1),
(2), (4) Date: Jul. 24, 2000

(87) PCT Pub. No.: WO99/28461

PCT Pub. Date: Jun. 10, 1999

(30) Foreign Application Priority Data

Dec. 3, 1997 (EP) ............................................. 97203783

(51) Int. Cl.$^7$ ............................. C12Q 1/00; C12Q 1/68; C12P 21/06; C12N 15/63
(52) U.S. Cl. ............................. 435/4; 435/6; 435/69.1; 435/455
(58) Field of Search ................................ 435/69.6, 325, 435/4, 6, 455; 424/186.1

(56) References Cited

U.S. PATENT DOCUMENTS

| 4,912,040 A | * | 3/1990 | Kaufman et al. | .......... | 435/69.1 |
| 5,196,523 A | | 3/1993 | Lee | ........................... | 536/23.5 |

FOREIGN PATENT DOCUMENTS

| WO | WO 94/08012 | 4/1994 |
| WO | WO 95/03414 | 2/1995 |
| WO | WO 97/25423 | 7/1997 |

OTHER PUBLICATIONS

Jacquier–Sarlin et al (Biochem and Biophys Res. Comm., 1996, vol. 226:166–71).*
Liston, et al, Nature, vol 379, 1996, pp. 349–353.*
Aoki, et al., *J. of Biochem.* (1997), 121:122–7.
Campbell, et al., *Genes and Development* (1997), 11:1098–10.
Danen–Van Oorschot, et al., *Apoptosis* (1997), 2:395–402.
Danen–Van Oorschot, et al., *Proc. Natl. Acad. Sci. USA* (1997), 94:5843–7.
Gazit, et al., *Cancer Res.* (1995), 55:1660–3.
Jamora, et al., *Proc. Natl. Acad. Sci. USA* (1996), 93:7690–4.
Lee, *Curr. Opin. Cell Biol.* (1992), 4:267–73.
Levine, *Cell* (1997), 88:323–31.
Matsudaira, *Seminars in Cell Biol.* (1994), 5:165–74.
Murthy, et al., *DNA and Cell Biol.* (1996), 15:727–35.
Noteborn, et al., *J. of Virology* (1991), 65:313–9.
Noteborn, et al., *J. of Virology* (1994), 68:346–51.
Noteborn, et al., *J General Virology* (1998), 79:3073–7.
Schlenstedt, et al., *J Cell Biol* (1995), 129:979–88.
Srinivasan, et al., *Molecular and Cell. Biol.* (1997), 17:4761–73.
Sugawara, et al., *Can. Res.* (1993), 53:6001–5.
Ting, et al., *Gene* (1987), 55(1):147–52.
Zhuang, et al., *Leukemia* (1995), 9(1):118–120.
Zhuang, et al., *Cancer Res.* (1995), 55:486–9.

* cited by examiner

*Primary Examiner*—Anthony C. Caputa
*Assistant Examiner*—Gary B. Nickol
(74) *Attorney, Agent, or Firm*—TraskBritt

(57) ABSTRACT

The invention relates to activation of apoptosis by means of interference of the function of Bip-like compounds. Also the invention relates to anti-tumor therapies with compounds, which negatively interfere with Bip-like compounds leading to induction of apoptosis, resulting in the elimination of tumor cells. Also the invention relates to therapies for diseases related to aberrant apoptosis induction, such as auto-immune diseases. Also the invention describes the diagnosis of cells, which are susceptible to apoptin or apoptin-like induced apoptosis.

6 Claims, 11 Drawing Sheets

CAGCTTCTGATAATCAACCAACTGTTACAATCAAGGTCTATGAAGGTGAAAGACCCCTGACAAAA
GACAATCATCTTCTGGGTACATTTGNTCCGACTGGAATTCCTCCTGCTCCTCGTGGGGTCCCACA
GATTGAAGTCACCTTTGAGATAGATGTGAATGGTATTCTTCGAAGTGACAGCTGANGACAAGGGT
ACAGGGAACANAAATAAGATCACAATCACCAATGACCAGAATCGCCTGACACCTGAAGAAATCNA
AAGGNTGGTTAATGATGCTGAGAATTTTGCTGAGGAAGACAAAAANCTCAAGGANCGCATTGATA
CTAGAAATGANTTGGAAANCTATGCCNATTCTCTAAAGAATCAGATTGGNGATAANGAAAANCTG
GAAGGTAAACTTTCCTCGGAANATANGGANACCATGGAAAAACNTGTNNAAAGAAAAATTTNGAN
TGGNTGGAAAANCAACCAATATGCNGACTTNNAAANTTCAANGNTAAGANNAGGGAANTGGGAAN
AATTTTTCACCCATTTTNCNAGNANACCCTANGNANTTNNAAGGCCCCCCCCCAATTNGGTANAG
GGGTTCCACCANAANAAATNGTTTTNTCACNCGGTTTCNGANNNGNCTNTTAANNTTGTAAAATN
GGGGCCCCNTT

Figure 1

```
CAGCTTCTGATAATCAACCAACTGTTACAATCAAGGTCTATGAAGGTGAAAGACCCCTGACAAAA
GACAATCATCTTCTGGGTACATTTGATCTGACTGGAATTCCTCCTGCTCCTCGTGGGGTCCCACA
GATTGAAGTCACCTTTGAGATAGATGTGAATGGTATTCTTCGAGTGACAGCTGAAGACAAGGGTA
CAGGGAACAAAAATAAGATCACAATCACCAATGACCAGAATCGCCTGACACCTGAAGAAATCGAA
AGGATGGTTAATGATGCTGAGAAGTTTGCTGAGGAAGACAAAAAGCTCAAGGAGCGCATTGATAC
TAGAAATGAGTTGGAAAGCTATGCCTATTCTCTAAAGAATCAGATTGGAGATAAAGAAAAGCTGG
GAGGTAAACTTTCCTCTGAAGATAAGGAGACCATGGAAAAAGCTGTAGAAGAAAAGATTGAATGG
CTGGAAAGCCACCAAGATGCTGACATTGNAGACTTCAAAGCTAANAANGAAGGAACTGGNANAAA
TTGTTCANCCAATTATCAGCAAACTCCAATGGAAGTGCAAGCCCTCCCCCAACTGGTGAAGANGA
TACAANCANGAAAAAGATGAGTTGTTACACTGATCTT
```

Figure 2

```
CTGATAATCAACCAACTGTTACAATCAAGGTCTATGAAGGTGAAAGACCCCTGANAAAAGACAAT
CATCTTCTGGGTACATTTGATTTGACAAACATTCNTCCTGCTCCTCGTGGGGTCCCACAGATTGA
TNGTCACCTTTGAGATAGATGTGAATGGTATTCTTCGAGTGACANNNTGANCGACAAGGGTACAG
GGAANAAAACTAAGATCANANTCACCAAATGATCAANAATCGNCTGANACCTGANGAAATNGAAA
GGATGGTTAATGATGCTGANGAAGTTTGCTGAGGAANACANAAAGCTCAAGGAGCGNATTGATAT
TAGAAGTGAGTTNGAAAGCTATGCCTATTCTCTATAGAATCAGATTGGNGATNATTGAANAGCTG
GGAGGTNAANTTCCTCNGATAGATNAGGANNANNATNGAANGAAGCTGTANTNGNAAANGATTGA
NATNGGCTGGAAANGCTNNCAAAGNATGCTTAACATTGNAAGGACTTNAATAGCTTAANNNANAA
GNGTACTGGGTATAAAANTNGTTCANCCANNTTATCATCANGTTTNCATNGGAANGTGNAANGGN
NCTNCTCGNNAACTGGGTGANTNAGGTTTCANCAAGANAAANTATTAAGTTTGNTAGNNACNGGA
TCTGGNTANGTGNCTGTANAANTGGTNTANTACGGNGNCTCAANGGAACTTAG
```

Figure 3

```
GGCCACGAAGGCCCACAGTGGTGCCTACCAAGAAGTCTCAGATCTTTTCTACAGCTTCTGATAAT
CAACCAACTGTTACAATCAAGGTCTATGAAGGTGAAAGACCCCTGACAAAAGACAATCATCTTCT
GGGTACATTTGATCTGACTGGAATTCCTCCTGCTCCTCGTGGGGTCCCACAGATTGAAGTCACCT
TTGAGATAGATGTGAATGGTATTCTTCGAGTGACAGCTGAAGACAAGGGTACAGGGAACAAAAAT
AAGATCACAATCACCAATGACCAGAATCGCCTGACACCTGAAGAAATCGAAAGGATGGTTAATGA
TGCTGAGAAGTTTGCTGAGGAAGACAAAAAGCTCAANGAGCGCATTGATACTAAGAAATGAGTTG
GAAAGCTATGCCTATTCTCTAAAGAATCAGATTGGNGATAAANAAAAGCTGGGAGGTAAACTTTC
CTCTGAAGATAAGGAGACCATGGAAAAAGCTGTAGAAGAAAAGATTGAATGGCTGGAAAGCCACC
ATGATGCTGACATTGAAGACTTCAAAGCTAAGAAGAAGAACTGGAAGAAATTGTTCAACCAATTA
TCAGCAAACTCTATGGGAANTGNAGGCCTCCCT
```

Figure 4

```
CTGATAATCAACCAACTGTTACAATCAAGGTCTATGAAGGTGAAAGACCCCTGACAAAAGACAATCATCTTC
TGGGTACATTTGATCTGACTGGAATTCCTCCTGCTCCTCGTGGGGTCCCACAGATTGAAGTCACCTTTGAGA
TAGATGTGAATGGTATTCTTCGAGTGACAGCTGAAGACAAGGGTACAGGGAACAAAAATAAGATCACAATCA
CCAATGACCAGAATCGCCTGACACCTGAAGAAATCGAAAGGATGGTTAATGATGCTGAGAAGTTTGCTGAGG
AAGACAAAAGCTCAAGGAGCGCATTGATACTAGAAATGAGTTGGTAAGCTATGCCTATTCTCTAAAGAATCA
GATTGGTGATAAAGAAAAGCTGGGAGGTAAACTTTCCTCTGAAGATAATGAGACCATGGAAAAAGCTGTAGA
AGAAAAGATTGAATGGCTGGAAAGCCACCAANATGCTGACATTGAAGACTTCANAGCTAAGANNAATGNACT
GGAAGAAATTGTTCAACCAANTATCAGCAAACTCTATGGAAGTGCAGGCCCTCCCCCAACCGGTGAATATGG
TACAGCAGAAAAAGATGAGTTNTANANACTGATCTGCTANTTG
```

Figure 5

```
c10/#1    1  ----------------------------------------WN DPRC HEGPASDNQPTV
c31/#2    1  ------------------------------------------------HEGPASDNQPTV
HumBip  401  AGVLSGDQDTGDLVLLHVCPLTLGIETVGGVMTKLIPSM TVVPTK SQIFST ASDNQPTV
c41/#3    1  ------------------------------------HEGRPRRP TVVPTK SQIFST ASDNQPTV
c45/#4    1  ----------------------------------------------HE PDNQPTV
c34/#5    1  ----------------------------------------------HE PDNQPTV c10/#1   21  TIKVYEGERPLTKDNHLLGTF VP TGIPPAPRGVPQIEVTFEIDVNGILR SD . --------
c31/#2   13  TIKVYEGERPLTKDNHLLGTFDLTGIPPAPRGVPQIEVTFEIDVNGILRVT . AEDKGTGN
HumBip  461  TIKVYEGERPLTKDNHLLGTFDLTGIPPAPRGVPQIEVTFEIDVNGILRVT . AEDKGTGN
c41/#3   30  TIKVYEGERPLTKDNHLLGTFDLTGIPPAPRGVPQIEVTFEIDVNGILRVT . AEDKGTGN
c45/#4   11  TIKVYEGERPLTKDNHLLGTFDLTGIPPAPRGVPQIEVTFEIDVNGILRVT . AEDKGTGN
c34/#5   11  TIKVYEGERPL KDNHLLGTFDLT I PAPRGVPQI IEL*DRCEWYSSSDXX DKGTG c10/#1   73  -----------------------------------------------------------
c31/#2   72  KNKITITNDQN . RLTPEEIERMVNDAEKFAEEDKKLKERIDTRNELESYAYSLKNQIGDK
HumBip  520  KNKITITNDQN . RLTPEEIERMVNDAEKFAEEDKKLKERIDTRNELESYAYSLKNQIGDK
c41/#3   89  KNKITITNDQN . RLTPEEIERMVNDAEKFAEEDKKL ERIDT K* GKLCLF K SDWI*
c45/#4   70  KNKITITNDQN . RLTPEEIERMVNDAEKFAEEDK SS SA ILEMSW* MPIL* IR VI
c34/#5   70  KTKI XX K* SXII* XLXKXKGW MMLX KFAEEXX KLKERID R EXESYAYSL* NQIGDX c10/#1   73  -----------------------------------------------------------
c31/#2  131  EKLGGKLSSEDKETMEKAVEEKIEWLESHQDADIV DFKA E GTGIMCSSHYQQTP MEVQ
HumBip  579  EKLGGKLSSEDKETMEKAVEEKIEWLESHQDADI DFKA KK LEEIVQPIISKLY GSAG
c41/#3  146  X AGR*TFL*R*GDHG K CRR D*MAGKPP*C*H*RLQ * EELEEIVQPIISKLY GXIR
c45/#4  127  KSWEVMFPLKIMRPWK L*KK ENGWK TIMLT KTSILRXMXWKK FQ . IS ANS MEVQ
c34/#5  127  *XA GRXX SS RIGXXXXEAVXXX * XXLEXLXKIA* HXK XNS XXKITGYXXXSXXLSS c10/#1   73  -----------------------------------------------------------
c31/#2  191  ALPQLVK Q S---------------------------------------
HumBip  639  PP TGEEDTAE DEL---------------------------------
c41/#3  198  PP------------------------------------------------
c45/#4  185  ALPQ V QQ KMSXXX*SAX-----------------------
c34/#5  184  XXHXX XXXX S XTG*XRFXQXXXLSLXXTGSGXVXVXXVXYGXSXEL
```

Figure 6

```
Filamin   1   RLRNGHVGISFVPKETGEHLVHVKKNGQHVASSPIPVVISQSEIGDASRVRVSGQGLHEG
c50/#1    1   ------------------------------------------------------------
c57/#2    1   ------------------------------------------------------------

Filamin  61   HTFEPAEFIIDTRDAGYGGLSLSIEGPSKVDINTEDLEDGTCRVTYCPTEPGNYIINIKF
c50/#1    1   ------------------------------------------------------------
c57/#2    1   -----------------------------------------HEGRPTEPGNYIINIKF Filamin 121   ADQHVPGSPFSVKVTGEGRVKESITRRRRAPSVANVGSHCDLSLKIPEISIQDMTAQVTS
c50/#1    1   ------------------------------------------------------------
c57/#2   18   ADQHVPGSPFSVKVTGEGRVKESITRRHRAPSVANVGSHCDLSLKIPEISIQDMTAQVTS Filamin 181   PSGKTHEAEIVEGENHTYCIRFVPAEHGTHTVSVKYKGQHVPGSPFQFTVGPLGEGGAHK
c50/#1    1   ------------------------------------------------------------
c57/#2   78   PSGKTHEAEIVEGENHTYCIRFVPAEHGTHTVSVKYKGQHVPGSPFQFTVGPLGEGGAHK Filamin 241   VRAGGPGLEEEEGVPEEFS.EWTREAGAGELAEAVEEPEKAEISFEDREDESCGEAYEV
c50/#1    1   ------------------------------------------------------------
c57/#2  138   VRAGGPGLEKE*EWSAERIQYEGPGKLVLEEWPELSXEPEXLXSLLRTAETEPVVELMEV Filamin 300   QEEGDYEVSVKFNEEHIPDSPFVVPVASPSGDARRLTVSSLQESGLKVNQPASFAVSLNG
c50/#1    1   ------------------------------------------------------------
c57/#2  197   XEPSE*XNPXQVSTKEHX------------------------------------------

Filamin 360   AKGAIDAKVHSPSGALEECYVTEIDQDKYAVRFIPRENGVYLIDVKFNGTHIPGSPFKIR
c50/#1    1   ------------------------------------------------------------
c57/#2  214   ------------------------------------------------------------

Filamin 420   VGEPGHGGDPGLVSAYGAGLEG.GVTGNPAEFVVNTSNAGAGALSVTIDGPSKVKMDCQE
c50/#1    1   ------------------HEGRGVTGNPAEFVVNTSNAGAGALSVTIDGPSKVKMDCQE
c57/#2  214   ------------------------------------------------------------

Filamin 479   CPEGYRVTYTPMAPGSYLISIKYGGPYHIGGSPFKAKVTGPRLVSNHSLHETSSVFVDSL
c50/#1   42   CPEGYRVTYTPMAPGSYLISIKYGGPYHIGGSPFKAKVTGPRLVSNHSLHETSSVFVDSL
c57/#2  214   ------------------------------------------------------------

Filamin 539   TKATCAPQHGAPGPGPADASKVVAKGLGLSKAYVGQKSSFTVDCSKAGNNMLLVGVHGPR
c50/#1  102   TKATCAPEHGAPGPGPADASKVVAKGLGLSKAYVCEKSSFTVDCSKACIIMLLVGVHGPW
c57/#2  214   ------------------------------------------------------------

Filamin 599   TPCEEILVKHVGS.REYSVSYLLKDKGE.YTLVVKWGHEHIPGSEYREVVP-
c50/#1  162   TPCDEILVKARGQPALQRVLTCFKDKGEVEGGQNGEDYQIPCKELPECGCP
c57/#2  214   ---------------------------------------------------
```

Figure 7

```
c23/#2    1   --------------------HEGRGVPEDLLNGLKVTDTQEAECAGPPVPDPKNQHSQSKLL
Trp-1     1   ----------------MGEKSENCGVPEDLLNGLKVTDTQEAECAGPPVPDPKNQHSQSKLL
c12/#1    1   ---HEGPSPPSLGSMGEKSENCGVPEDLLNGLKVTDTQEAECAGPPVPDPKNQHSQSKLL
c32/#4    1   -HEGPLASPPSLGSMGEKSENCGVPEDLLNGLKVTDTQEAECAGPPVPDPKNQHSQSKLL
c27/#3    1   HEGXSLXSPPSLGSMGEKSENCGVPEDLLNGLKVTDTQEAECAGPPXPDPKNQHSQSKLL c23/#2   43   RDDEAHLQEDQGEEECFHDCSASFEEEPGADKVENKSNEDVNSSELDEEYLIELEKNMSD
Trp-1    47   RDDEAHLQEDQGEEECFHDCSASFEEEPGADKVENKSNEDVNSSELDEEYLIELEKNMSD
c12/#1   58   RDDEAHLQEDQGEEECFHDCSASFEEEPGADKVENKSNEDVNSSELDEEYLIELEKNMSD
c32/#4   60   RDDEAHLQEDQGEEECFHDCSASFEEEPGADKVENKSNEDVNSSELDEEYLIELEKNMSD
c27/#3   61   RDDEAHLQEDQGEEECFHDCSASFEEEPGADVVENKSNEDVNSSELQEEYLIQLEKNMSD c23/#2  103   EEKQKRREESTRLKEEGNEQFKKGDYIEAESSYSRALEMCPSCFQK.ERSILFSNRAAAR
Trp-1   107   EEKQKRREESTRLKEEGNEQFKKGDYIEAESSYSRALEMCPSCFQK.ERSILFSNRAAAR
c12/#1  118   EEKQKRREESTRLKEEGNEQFKKGDYIEAESSYSRALEMCPSCFQK.ERSIXFSNRAAAR
c32/#4  120   EEKQKRREESTXLKEEGNEQFKKGDYIXAESSYSRALEMCPSCFQK.EXSILFSNTAAAX
c27/#3  121   EEKXKRRXXSTRLKXEGNEQFKKGDYIEAESSYKSEPRNVPILLPKXEVDSEFXYSCEKG c23/#2  162   MKQDKKEMAINDCSLAIQLNPSYIRAILRRAEV*--------------------------
Trp-1   166   MKQDKKEMAINDCSKAIQLNPSYIRAILRRAELYEKTDKLDEALEDYKSILEKDPSIHQA
c12/#1  177   MXQDKKEMAIXDCSKAFN*TPAISXQY*GXQXCHRXRTS*XXPWM---------------
c32/#4  179   DXTGQEXNQHPMTXXLQFN*PHLYXGXEXDXM----------------------------
c27/#3  181   *NMXXKKWXSXDCSKAPX*TPTYXINEXDIRVXX-------------------------- c23/#2  196   ------------------------------------------------------------
Trp-1   226   REACMRLPKQIEERNERLKEEMLGKLKDLGNLVLRPFGLSTENFQIKQDSSTGSYSINFV
c12/#1  219   ------------------------------------------------------------
c32/#4  210   ------------------------------------------------------------
c27/#3  213   ------------------------------------------------------------ c23/#2  196   ------
Trp-1   286   QNPNNNR
c12/#1  219   ------
c32/#4  210   ------
c27/#3  213   ------
```

Figure 8

```
GTGATATTATTGTAGATCTAGAAGTCACTTTGGAAGAAGTATATGCAGGAAATTTTGTGGAAGTA
GTTAGAAACAAACCTGTGGCAAGGCAGGCTCCTGGCAAACGGAAGTGCAATTGTCGGCAAGAGAT
GCGGACCACCCAGCTGGGCCCTGGGCGCTTCCAAATGACCCAGGAGGTGGTCTGCGACGAATGCC
CTAATGTCAAACTAGTGAATGAAGAACGAACGCTGGAAGTAGAAATAGAGCCTGGGGTGAGAGAC
GGCATGGAGTACCCCTTTATTGGAGAAGGTGAGCCTCACGTGGATGGGGAGCCTGGAGATTTACG
GTTCCGAATCAAAGTTGTCAAGCACCCAATATTTGAAAGGAGAGGAGATGATTTGTACACAAATG
TGACAATCTCATTAGTTGAGTCACTGGTTGGCTTTGAGATGGATATTACTCACTTGGATGGTCAC
AAGGTACATATTTCCCGGGATAAAGATCACCAGGCCANGAGCGAATCTATGGAANAAAGGGGAAG
GGCTCCCCAACTTTGACAACAACAATATCAAGGGCTCCTTGATAATCACTTTTGANGTGGATTTT
TCCANAAGAACAGTTACAGAGGAAGCCANAGAAGTATCAAAACANCTACTNAAACAAAGTCAATT
CAGAAGNNTNCAATGGACCGCAANGATTTGAAAANTGAATAAATTGNCNTTGTTAAAATAATTNA
TTANCCATNATTATNANTCAAGGTTTTTTT
```

Figure 9

METHODS AND MEANS FOR INDUCING APOPTOSIS BY INTERFERING WITH BIP-LIKE PROTEINS

CROSS-REFERENCE TO RELATED APPLICATIONS

This application is a §371 filing of PCT/NL98/00688, filed Dec. 3, 1998, which claims priority from European Patent Application No. 97203783.2, filed Dec. 3, 1997.

The present invention relates to the field of apoptosis, as well as to the field of cancer diagnosis and treatment, and treatment and diagnosis of auto-immune diseases and other diseases by induction of apoptosis. In particular the invention provides novel molecules and means to induce apoptosis or enhance apoptosis. The novel molecules and means are part of the apoptotic pathway induced by apoptin. Apoptin is a protein originally found in chicken anemia virus (CAV; Noteborn et al., 1991) and was originally called VP3. The apoptotic activity of this protein was discovered by the group of the present inventors (Noteborn et al., 1994).

As stated above the present invention makes use of the induction of apoptosis in which Bip-like proteins are involved.

Apoptosis is an active and programmed physiological process for eliminating superfluous, altered or malignant cells (Earnshaw, 1995, Duke et al., 1996). Apoptosis is characterized by shrinkage of cells, segmentation of the nucleus, condensation and cleavage of DNA into domain-sized fragments, in most cells followed by internucleosomal degradation. The apoptotic cells fragment into membrane-enclosed apoptotic bodies. Finally, neighbouring cells and/or macrophages will rapidly phagocytose these dying cells (Wyllie et al., 1980, White, 1996). Cells grown under tissue-culture conditions and cells from tissue material can be analysed for being apoptotic with agents staining DNA, as e.g. DAPI, which stains normal DNA strongly and regularly, whereas apoptotic DNA is stained weakly and/or irregularly (Noteborn et al., 1994, Telford et al., 1992).

The apoptotic process can be initiated by a variety of regulatory stimuli (Wyllie, 1995, White 1996, Levine, 1997). Changes in the cell survival rate play an important role in human pathogenesis, e.g. in cancer development, which is caused by enhanced proliferation but also by decreased cell death (Kerr et al., 1994, Paulovich, 1997). A variety of chemotherapeutic compounds and radiation have been demonstrated to induce apoptosis in tumor cells, in many instances via wild-type p53 protein (Thompson, 1995, Bellamy et al., 1995, Steller, 1995, McDonell et al., 1995).

Many tumors, however, acquire a mutation in p53 during their development, often correlating with poor response to cancer therapy. Transforming genes of tumorigenic DNA viruses inactivate p53 by directly binding to it (Teodoro, 1997). An example of such an agent is the large T antigen of the tumor DNA virus SV40. For several (leukemic) tumors, a high expression level of the proto-oncogene Bcl-2 or Bcr-abl is associated with a strong resistance to various apoptosis-inducing chemotherapeutic agents (Hockenberry 1994, Sachs and Lotem, 1997).

For such cancers (representing more than half of the tumors) alternative anti-tumor therapies are under development based on induction of apoptosis independent of p53 (Thompson 1995, Paulovich et al., 1997). One has to search for the factors involved in induction of apoptosis, which do not need p53 and/or can not be blocked by Bcl-2/Bcr-abl-like anti-apoptotic activities. These factors might be part of a distinct apoptosis pathway or being (far) downstream to the apoptosis inhibiting compounds.

Apoptin is a small protein derived from chicken anemia virus (CAV; Noteborn and De Boer, 1995, Noteborn et al., 1991, Noteborn et al., 1994), which can induce apoptosis in human malignant and transformed cell lines, but not in untransformed human cell lines. In vitro, apoptin fails to induce programmed cell death in normal lymphoid, dermal, epidermal, endothelial and smooth-muscle cells. However, when normal cells are transformed they become susceptible to apoptosis by apoptin. (Danen-van Ooschot, 1997 and Noteborn, 1996). Long-term expression of apoptin in normal human fibroblasts revealed that apoptin has no toxic or transforming activity in these cells.

In normal cells, apoptin was found predominantly in the cytoplasm, whereas in transformed or malignant cells i.e. characterized by hyperplasia, metaplasia or dysplasia, it was located in the nucleus, suggesting that the localization of apoptin is related to its activity (Danen-van Oorschot et al. 1997).

Apoptin-induced apoptosis occurs in the absence of functional p53 (Zhuang et al., 1995a), and cannot be blocked by Bcl-2, Bcr-abl (Zhuang et al., 1995), the Bcl-2-associating protein BAG-1 and not by the caspase-inhibitor cowpox protein CrmA (Danen-Van Oorschot, 1997a, Noteborn, 1996).

Therefore, apoptin is a potent agent for the destruction of tumor cells, or other hyperplasia, metaplasia or dysplasia which have become resistant to (chemo)therapeutic induction of apoptosis, due to the lack of functional p53 and (over)—expression of Bcl-2 and other apoptosis-inhibiting agents. (Noteborn et al., 1997).

The fact that apoptin does not induce apoptosis in normal human cells, at least not in vitro, suggests that a toxic effect of apoptin treatment in vivo will be very low. Noteborn et al. (1997) have provided evidence that adenovirus expressed apoptin does not have an acute toxic effect in vivo. In addition, in nude mice it was shown that apoptin has a strong anti-tumor activity.

It appears, that even pre-malignant, minimally transformed cells, may be sensitive to the death-inducing effect of apoptin. In addition, Noteborn and Zhang (1997) have shown that apoptin-induced apoptosis can be used as diagnosis of cancer-prone cells and treatment of cancer-prone cells.

Knowing that apoptin is quite safe in normal cells, but that, as soon as, a cell becomes transformed and/or immortalized (the terms may be used interchangeable herein) the present inventors designed novel means and methods for the induction of apoptosis based on the identification of compounds involved in the apoptin-induced apoptotic cascade. These compounds are factors of an apoptosis pathway, which is specific for transformed cells. Therefore, these proteins are very important compounds in new treatments and diagnosis for diseases related with aberrancies in the apoptotic process, such as cancer, and auto-immune diseases.

A group of proteins found to be associated with the apoptotic pathway is the family of Bip-like proteins.

Thus the invention provides a recombinant and/or isolated nucleic acid molecule encoding at least a functional part of a member of the family of Bip/GRP78-like proteins comprising at least a functional and/or specific part of the sequence given in FIGS. 1, 2, 3, 4 or 5 or a sequence at least 70%, preferably 80, most preferably 90% homologous therewith. In one possible mechanism of action Bip-like proteins which are chaperones bind to apoptin or apoptin-like proteins resulting in a conformational change in the apoptin-like proteins resulting in enhanced apoptotic activity. Protein-like activity herein is defined as any molecule indirectly or directly providing similar activity as the original protein (in kind not necessarily in amount). It is preferred to bring the Bip-like activity into a cell, which can be done suitably using an expression vector. It is of course preferred if not required that such a cell is also provided with apoptotic, preferably apoptin-like activity. A very suitable manner is to provide apoptin-like activity on another or the same vector.

The invention also provides a recombinant and/or isolated proteinaceous substance having Bip/GRP78-like activity and comprising at least a functional part of the sequence of FIG. 6 or FIG. 7 or a functional equivalent thereof or being encoded by a nucleic acid molecule according to claim 1. Except as being used for enhancing apoptosis this proteinaceous substance can also be used to identify further apoptotic agents. Such agents are therefor also part of the present invention.

The invention further provides a method for inducing apoptosis in a cell comprising providing said cell with Bip/GRP78 inhibiting activity, preferably together with apoptin-like activity.

As stated the invention provides a method for inducing apoptosis through interference with the function of Bip-like proteins (interchangeably referred to as Bip or Bip-like proteins).

The invention provides an anti-tumor therapy based on the interference with the function of Bip-like proteins. The fact that Bip-like proteins are abundantly present in tumor cells in combination with highly-expressed oncogenes and that Bip associates with apoptin, makes Bip-like proteins very important targets of an anti-tumor agent.

The invention provides Bip as the mediator of apoptin-induced apoptosis, which is tumor-specific.

The invention will be explained in more detail in the following experimental part. This only serves for the purpose of illustration and should not be interpreted as a limitation of the scope of the invention.

BRIEF DESCRIPTION OF THE DRAWINGS

FIG. 1 shows the DNA sequence of the analysed region of the apoptin-associating clone Bip/GRP78 No-1 (SEQ ID NO: 1).

FIG. 2 shows the DNA sequence of the analysed region of the apoptin-associating clone Bip/GRP78 No-2 (SEQ ID NO:2)

FIG. 3 shows the DNA sequence of the analysed region of the apoptin-associating clone Bip/GRP78 No-3 (SEQ ID NO:3).

FIG. 4 shows the DNA sequence of the analysed region of the apoptin-associating clone Bip/GRP78 No-4 (SEQ ID NO:4).

FIG. 5 shows the DNA sequence of the analysed region of the apoptin-associating clone Bip/GRP78 No-5 (SEQ ID NO:5).

FIG. 6 shows the combination of the amino acids of the sequenced Bip-like clones No-1 through No-5 (SEQ ID NOs:6, 7 and 9–11). The fact that they overlap with each other implies that the common region of all five inserts will associate with apoptin. The amino acid sequence of the known Bip/GRP78 is also shown (SEQ ID NO:8). In addition, the three C-terminal amino acids H-E-G of the multiple cloning site of pACT are given to illustrate that the Bip/GRP78-like amino acid sequence is in frame with the GAL-activation domain. This feature proves that the Bip-GRP-like region is indeed synthesized.

FIG. 7 shows the amino acids of the sequenced region of the apoptin associating clone Filamin No-1 and No-2 (SEQ ID NO:13–). In addition, the three C-terminal amino acids H-E-G of the multiple cloning site of pACT are given to illustrate that the filamin-like amino acid sequence is in frame with the GAL4-activation domain. This feature proves that the filamin-like region is indeed synthesized. The amino acid sequence of the known Filamin is also shown (SEQ ID NO: 12).

FIG. 8 shows the amino acid sequence, derived frm the analysed region of the apoptin-associating clones TRP-1 No 1 through No4 (SEQ ID NOs:15 and 17–19). Also, the known TRP-1 (EMBL/Genbank) is shown (SEQ ID NO:16).

FIG. 9 shows the DNA sequence of the analysed region of the apoptin-associating clone DNAJ-like protein (SEQ ID NO:20).

EXPERIMENTAL PART

Figure 10:
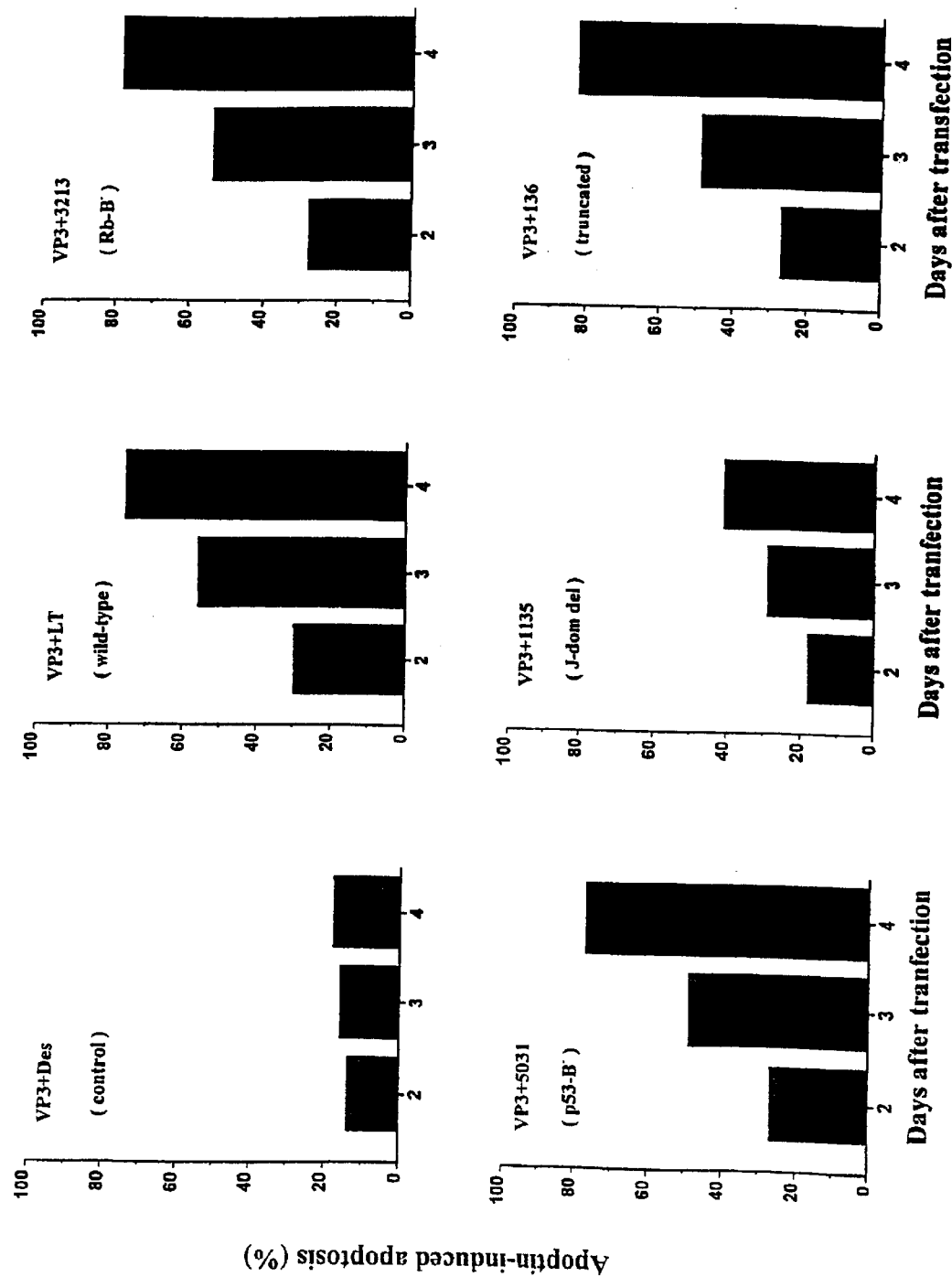
FIG. 10 shows the induction of apoptosis due to co-expression in normal non-transformed VH10 cells of Apoptin and Desmin (VP3+des; negative control), wild-type SV40 LT (VP3+LT), LT-mutant lacking the retinoblastoma-binding site (VP3+3213), LT-mutant missing the p53-binding sites (VP3+5031), LT-mutant with a deletion in the J domain (VP3+1135), and LT-mutant 136 containing almost only the J domain or a nuclear localization signal (VP3+136). Actually, the % of apoptosis observed with desmin and Apoptin resembles the background level due to the transfection procedures (Danen-Van Oorschot, 1997).

The inventors have used the yeast-2 hybrid system (Durfee et al., 1993) to identify apoptin-associating cellular compounds, that are essential in the induction of apoptosis. The used system is an in-vivo strategy to identify human proteins capable of physically associating with apoptin. It has been used to screen cDNA libraries for clones encoding proteins capable of binding to a protein of interest (Fields and Song, 1989, Yang et al., 1992).

Construction of pGBT9-VP3

For the construction of the bait plasmid, which enables the identification of apoptin-associating proteins by means of a yeast-two-hybrid system, plasmid pET-16b-VP3 (Noteborn, unpublished results) was treated with NdeI and BamHI. The 0.4 kb NdeI-BamHI DNA fragment was isolated from low-melting-point agarose.

Plasmid pGBT9 (Clontech Laboratories, Inc, Palo Alto, USA) was treated with the restriction enzymes EcoRI and BamHI. The about 5.4 kb DNA fragment was isolated and ligated with an EcoRI-NdeI linker and the 0.4-kb NdeI-BamHI DNA fragment containing the apoptin-encoding sequences starting from its own ATG-initiation codon. The final construct containing a fusion gene of the GAL4-binding domain sequence and apoptin under the regulation of the yeast promoter ADH was called pGBT-VP3 and was proven to be correct by restriction-enzyme analysis and DNA-sequencing according to the Sanger method (1977).

All cloning steps were essentially carried out as described by Maniatis et al. (1992). The plasmid pGBT-VP3 was prurified by centrifugation in a CsCl gradient and column chromatography in Sephacryl S500 (Pharmacia).

GAL4-activation domain-tagged CDNA libraries

The expression vector pACT, containing the cDNAs from Epstein-Barr-virus-transformed human B cells fused to sequences for the GAL4 transcriptional activation domain, was used for detecting apoptin-associating proteins. The pACT c-DNA library is derived from the lambda-ACT cDNA library, as described by Durfee et al. 1993.

Bacterial and Yeast Strains

The *E.coli* strain JM109 was the transformation recipient for the plasmid pGBT9 and pGBT-VP3. The bacterial strain Electromax/DH10B was used for the transformation needed for the recovery of the apoptin-associating pACT-cDNAs, and was obtained from GIBCO-BRL, USA).

The yeast strain Y190 was used for screening the cDNA library, and all other transformations which are part of the used yeast-two-hybrid system.

Media

For drug selections Luria Broth (LB) plates for *E.coli* were supplemented with ampicillin (50 microgram per ml). Yeast YPD and SC media were prepared as described by Rose et al. (1990).

Transformation of Competent Yeast Strain Y190 with Plasmids pGBT-VP3 and pACT-cDNA and Screening for Beta-galactosidase Activity The yeast strain Y190 was made competent and transformed according to the methods described by Klebe et al. (1983). The yeast cells were first transformed with PGBT-VP3 and subsequently transformed with pACT-cDNA, and these transformed yeast cells were grown on histidine-minus plates, also lacking leucine and tryptophan.

Hybond-N filters were layed on yeast colonies, which were histidine-positive and allowed to wet completely. The filters were lifted and submerged in liquid nitrogen to permeabilize the yeast cells. The filters were thawed and layed with the colony side up on Whattman 3 MM paper in a petridish with Z-buffer (Per liter: 16.1 gr $Na_2HPO_4.7H_2O$, 5.5 gr $NaH_2PO_4$. $H_2O$, 0.75 gr KCl and 0,246 gr $MgSO_4.7H_2O$, pH 7.0) containing 0.27% beta-mercaptoethanol and 1mg/ml X-gal. The filters were incubated for at least 15 minutes or overnight.

Recovery of Plasmids From Yeast

Total DNA from yeast cells, which were histidine- and beta-galactosidase-positive was prepared by using the glusulase-alkaline lysis method as described by Hoffman and Winston (1987) and used to transform Electromax/DH10B bacteria via electroporation using a Bio-Rad GenePulser according the manufacturer's specifications.

Transformants were plated on LB media containing ampicillin.

Isolation of Apoptin-associating pACT Clones

By means of a colony-filter assay the colonies were lysed and hybridized to a radioactive-labeled 17-mer oligomer, which is specific for pACT (see section entitled Sequence analysis).

DNA was isolated from the pACT-positive clones, and by means of XhoI digestion analysed for the presence of a cDNA insert.

Sequence Analysis

The subclones containing the sequences encoding apoptin-associating proteins were sequenced using dideoxy NTPs according to the Sanger method, which was performed by EuroGentec Nederland BV (Maastricht, The Netherlands). The used sequence primer was a pACT-specific 17-mer comprising the DNA-sequence 5'-TACCACTACAATGGATG-3' (SEQ ID NO:21).

The sequences of the apoptin-associating proteins were compared with known gene sequences from the EMBL/Genbank.

Results and Discussion

Apoptin specifically induces apoptosis in transformed cells, such as cell lines derived from human tumors. To identify the essential compounds in this cell-transformation-specific and/or tumor-specific apoptosis pathway, a yeast genetic screen was carried out.

We have used a human cDNA library, which is based on the plasmid vector pACT containing the complete cDNA copies made from Epstein-Barr virus-transformed human B cells (Durfee et al., 1993).

Construction of a Bait Plasmid Expressing a Fusion-gene Containing a GAL4 DNA-binding Domain and Apoptin To examine the existence of apoptin-associating proteins in the human transformed/tumorigenic cDNA library, a so-called bait plasmid had to be constructed.

To that end, the complete apoptin-encoding region, flanked by about 40 basepairs downstream from the apoptin gene, was cloned in the multiple cloning site of plasmid pGBT9.

The final construct, called pGBT-VP3, was analysed by restriction-enzyme analysis and sequencing of the fusion area between apoptin and the GAL4-DNA-binding domain.

A Gene(fragment) Encoding an Apoptin-associating Protein is Determined by Transactivation of a GAL4-responsive Promoter in Yeast The apoptin gene is fused to the GAL4-DNA-binding domain of plasmid pGBT-VP3, whereas all cDNAs derived from the transformed human B cells are fused to the GAL4-activation domain of plasmid pACT. If one of the cDNAs will bind to apoptin, the GAL4-DNA-binding domain will in the vicinity of the GAL4-activation domain resulting in the activation of the GAL4-responsive promoter, which regulates the reporter genes HIS3 and LacZ.

The yeast clones containing plasmid expressing apoptin and a plasmid expressing an apoptin-associating protein (fragment) can grow on a histidine-minus medium and will stain blue in a beta-galactosidase assay. Subsequently, the plasmid with the cDNA insert encoding the apoptin-associating protein can be isolated and characterized.

We have determined that transformation of yeast cells with pGBT-VP3 plasmid alone or in combination with an empty pACT vector, did not result in the activation of the GAL4-responsive promoter.

Identification of Apoptin-associating Proteins Encoded by cDNAs Derived from a Human transformed B Cell Line We have found yeast colonies, which upon transformation with pGBT-VP3 and pACT-cDNA were able to grow on a histidine-minus medium (also lacking leucine and tryptophan) and stained blue in a beta-galactosidase assay. These results indicate that these yeast colonies contain besides the bait plasmid pGBT-VP3 a pACT plasmid encoding for a potential apoptin-associating protein.

Plasmid DNA was isolated from these positive yeast colonies, which were transformed in bacteria. By means of a filter-hybridization assay using a pACT-specific labeled DNA-probe, the clones containing pACT plasmid could be determined. Subsequently, pACT DNA was isolated and digested with restriction enzyme XhoI, which is indicative for the presence of a cDNA insert. The pACT plasmids with a cDNA were sequenced.

Description of an Apoptin-associating Protein

The yeast genetic screen for apoptin-associating proteins resulted in the detection of Bip-like proteins (Bip is also called GRP78 protein).

The determined DNA sequences of the five independent Bip/GRP78 cDNA clones are shown in FIGS. 1–5, respectively. The combined amino acid sequence of all clones is given in FIG. 6, illustrating that they share a common region, which will be the part associating with apoptin.

Construction of an Expression Vector for the Identification of the Association of Apoptin and Bip/GRP78-like Proteins in Transformed Mammalian Cells To study the association of Apoptin and Bip/GRP78-like proteins in a mammalian cellular background, we have generated pSM2NT vectors containing the Bip/GRP78 cDNA inserts. Another important feature of this approach is that we can prove that the cloned cDNA indeed encodes an (Apoptin-associating) protein product.

The DNA plasmid pSM2NT contains the adenovirus 5 major late promoter (MLP) and the SV40 ori enabling high levels of expression of foreign genes in transformed mammalian cells, such as Cos cells.

Furthermore, the pSM2NT vector contains a Myc-tag (amino acids: EQKLISEEDL (SEQ ID NO:22)) which is in frame with the foreign-gene product. This Myc-tag enables the recognition of the e.g., Apoptin-associating proteins by means of th Myc-tag-specific 9E10 antibody.

The pSM2NT construct expressing Myc-tagged Bip/GRP78 was constructed as follows. The pACT-Bip/GRP78 clone no. 31 was digested with the restriction enzyme XhoI and the requested CDNA insert was isolated. The expression vector pSM2NT was digested with XhoI and treated with calf intestine alkline phosphatase and ligated to the subsequent isolated cDNA inserts. By sequence analysis, the pSM2NT clone containing the Bip/GRP78 cDNA in the correct orientation were identified.

The expression of the Myc-tagged Bip/GRP78 protein was analyzed by transfection of Cos cells with plasmid pSM2NT-Bip/GRP78. As negative control, Cos cells were mock-transfected.

Two days after transfection, the cells were lysed and Western-blot analysis was carried out using the Myc-tag-specific antibody 9E10. The Cos cells transfected with pSM2NT-Bip/GRP78 were proven to synthesize a specific Myc-tagged Bip/GRP78 product with the expected size of approximately 27 kDa. As expected, the lysates of the mock-transfected Cos cells did not contain a protein product reacting with the Myc-tag-specific antibodies.

These results indicate that we have been able to isolate a cDNA that indeed is able to produce a Bip/GRP78-like protein product with the ability to associate with the apoptosis-inducing protein Apoptin.

Co-immunoprecipitation of Myc-tagged Bip/GRP78 with Apoptin in a Transformed Mammalian Cell System Next, we have analyzed the association of Apoptin and Bip/GRP78 by means of co-immunoprecipitations using the Myc-tag-specific antibody 9E10. The 9E10 antibody was shown not to bind directly to Apoptin, which enables the use of 9E10 for carrying out co-immuno-precipitation assays with (myc-tagged) Apoptin-associating proteins and Apoptin. To that end, Cos cells were co-transfected with plasmid pCMV-VP3 encoding Apoptin and with plasmid pSM2NT-Bip/GRP78 encoding the Myc-tagged Bip/GRP78 protein. As negative control, we have transfected cells with Apoptin and a plasmid pSM2NT-LacZ encoding the myc-tagged beta-galactosidase, which does not associate with Apoptin.

Two days after transfection, the cells were lysed in a buffer consisting of 50 mM Tris (7.5), 250 mM NaCl, 5 mM EDTA, 0.1 % Triton X100, 1 mg/ml $Na_4P_2O_7$ and freshly added protease inhibitors such as PMSF, Trypsine-inhibitor, Leupeptine and $Na_3VO_4$. The specific proteins were immuno-precipitated as described by Noteborn et al. (1998) using the Myc-tag-specific antibodies 9E10, and analyzed by Western blotting.

Staining of the Western blot with 9E10 antibodies and 111.3 antibodies, which are specifically directed against Apoptin, showed that the 'total' cell lysates contained Apoptin and the Myc-tagged Bip/GRP78 or beta-galactosidase product. Immunoprecipitation of the Myc-tagged Bip/GRP78 products was accompanied by the immunoprecipatation of Apoptin product of 16 kDa. In contrast, immunoprecipitation of myc-tagged beta-galactosidase did not result in co-precipitation of the Apoptin protein.

In total, three independent immunoprecipitation experiments were carried out, which all showed the associating ability of Apoptin to the Bip/GRP78 proteins.

These results indicate that besides the yeast background, Bip/GRP78 is able to specifically associate with Apoptin in a mammalian transformed cellular system.

Characteristics of Bip/GRP78-like Proteins

Glucose regulated proteins are, like heat shock proteins, induced by stress. The most abundant glucose regulated protein is GRP78 (78 kD), also known as the immunoglobulin heavy chain binding protein Bip. It functions as a molecular chaperone and binds $Ca^{2+}$. It is expressed in many cell types and is located in the endoplasmic reticulum (ER; Lee, 1992).

Bip is permanently highly expressed in progressively growing tumors. Furthermore, Bip levels were increased in murine embryonic cells transformed by chemicals or radiation, and the level of Bip in fibrosarcomas was found to correlate with tumor growth (Gazit et al., 1995).

In Chinese hamster ovary cells, inhibition of Bip leads to increased cell death during chronic hypoxia or after treatment with a Ca2+ ionophore. In fibrosarcoma cells, Bip protects against cell lysis induced by cytotoxic T lymphocytes (CTLs) and tumor necrosis factor (TNF), suggesting that increased levels of Bip may protect tumor cells from immune attack in vivo (Sugawara et al., 1990).

In B/C10ME fibrosarcoma cells, inhibition of Bip by an anti-sense construct results in increased apoptotic cell death after Ca2+ depletion from the ER, but the in vitro growth rate is not affected. Upon injection of these cells in mice, no tumors were formed (Jamora et al., 1996).

Jamora et al. (1996) have suggested that suppression of Bip may be a new approach to cancer therapy. Their data, however, do not prove the application of such a therapy. The fact that Bip associates with apoptin, makes apoptin and/or Bip essential elements of a feasible anti-tumor therapy (Noteborn et al., 1997).

Therefore, the interference of Bip by, e.g. apoptin, in transformed cells is the crucial event during anti-tumor therapy. We have found an example of an effective regulator of Bip-like proteins, resulting in induction of apoptosis, which is the key to tumor rejection.

Induction of Apoptosis Through Interference of Bip-like Proteins

Our results indicate that apoptin can change and/or eliminate the Bip-like mediated activity, resulting in induction of apoptosis. This mechanism is one possibility of action (Jamora et al., 1996).

Bip-like proteins are chaperone proteins, which can influence the conformation of proteins and by doing so its function. Association of apoptin with Bip-like proteins will result in a change of its conformation and its function. Apoptin will be able to enter and/or to stay in the nucleus of (transformed) cells, and as a consequence the cell. will undergo apoptosis.

It is known that apoptin induces apoptosis preferentially in transformed cells and/or cells expressing transforming agents, most likely due to interaction with specific Bip-like proteins.

Co-expression of Bip-like Protein and Apoptin in Normal Cells Results in Induction of Apoptosis Next, we have examined the effect of expression of Bip-like proteins and apoptin on the induction of apoptosis in normal cells. To that end, VH10 and VH25 cells were transfected with plasmids encoding Bip-like protein and apoptin (Graham and Van der Eb, 1973). By immunofluorescence apoptin- and/or Bip specific monoclonal antibodies (Noteborn et al., Van den Heuvel, 1990) apoptin- and Bip-positive cells were detected.

The percentage of apoptotic cells within the group of apoptin and/or Bip-like protein-positive cells was detected staining the cells with DAPI (Danen-Van Oorschot et al., 1997, Telford et al., 1992). The normal fibroblasts expressing apoptin or Bip alone did not undergo apoptosis, whereas the cells co-expressing both apoptin and Bip did.

Factors that make use of interference with the function of Bip-like proteins, which results in induction of apoptosis are apoptin and apoptin-like proteins. Furthermore, it concerns proteins that are related to apoptin-induced apoptosis, such as the CAV-derived protein VP2, which is known to enhance apoptin-induced apoptosis (Noteborn et al., 1997).

Other Apoptin-associating Proteins

The genetic yeast screen with pGBT-VP3 as bait plasmid and pACT plasmid containing cDNAs from transformed human B cells also delivered the protein filamin. The protein filamin is localized within lamellipodia and filopodia. Filamin is one of the cross-linking proteins of actin. It may play an additional role of linking the cytoskeleton to cell-substratum adhesion sites (Matsudaira, 1994).

Two independent filamin-like clones were found. The found associating amino acid sequence of the two filamin clones are shown in FIG. 7.

To analyze into further detail the associating properties of Apoptin and filamin, we have co-expressed Myc-tagged filamin-like proteins by means of the pSM2NT vector (as described for Bip/GRP78) in Cos cells together with Apoptin.

Immunoprecipitation data clearly showed that 9E10 precipitates both filamin and Apoptin indicating that Apoptin associates to filamin in Cos cells. Our data indicate that Apoptin associates with filamin in both yeast and transformed mammalian cells.

Another apoptin-associating protein that was found is a TPR-1-like protein. In total four independent pACT-cDNA clones could be determined. TPR-1 (Murthy et al., 1996) was indentified by its ability to bind to neuro-fibromin. It contains three tandem tetratricotpeptide motifs (Blatch et al., 1997), but shows no homology outside this domain to other known proteins. The combined amino acid sequence of the observed TPR-1 clones is shown in FIG. 8.

Also, a human homolog of the bacterial chaperone DNAJ (Schlenstedt et al., 1995) was found as an apoptin-associating protein. The DNA sequence of the observed DNAJ-like clone is shown in FIG. 9.

To analyze into further detail the associating properties of Apoptin and this DNAJ-like protein, we initially have expressed Myc-tagged DNAJ-like cDNA (clone 26; see FIG. 9) by means of the pSM2NT vector (as described for Bip/GRP78) in Cos cells. Western-blot analysis using the Myc-tag-specific antibodies 9E10 showed a specific Myc-tagged DNAJ-like protein of 30 kDa. These results indicate that the isolated cDNA indeed encodes a protein of the expected size.

Next immunoprecipitation assays were carried out with transiently transfected Cos cells co-synthesizing Myc-tagged DNAJ and Apoptin. The results clearly showed that 9E10 precipitates both DNAJ-like proteins and Apoptin indicating that Apoptin associates with this new DNAJ-like protein in a mammalian transformed background. In total, three independent immunoprecipitation experiments were carried out, which all showed the associating ability of Apoptin to the DNAJ-like proteins.

In summary, our findings prove that our newly discovered DNAJ-like protein is able to associate to the apoptosis-inducing protein Apoptin in both a yeast and mammalian cellular background. Therefore, this DNAJ-like protein plays an important role in the induction of (Apoptin-regulated) apoptosis.

Other DNAJ-like Domains (indirectly) also Activate Apoptin-induced Apoptosis in Non-transformed Human Cells Co-expression of SV40 large T antigen (LT) and Apoptin results in apoptin-induced apoptosis in normal diploid cells derived from human individuals and rodents (Noteborn and Zhang, 1998). These data prove that diploid cells are not susceptible to Apoptin, whereas they become when they express a transforming protein.

In a new series of experiments, we have investigated the effect of mutations within SV40 LT on the level of Apoptin-induced apoptosis in normal diploid human fibroblasts.

To that end, human VH10 fibroblasts were co-transfected with plasmids encoding Apoptin and complete LT, LT-mutant 3213, lacking the Retinoblastoma-binding site, LT-mutant 5031 lacking pS53-binding sites, LT-mutant 1135 minus the J-domain or the LT-mutant 136 containing almost only the J-domain sequences and the nuclear location signal of SV40 (Srinivasan, 1997). This SV40 DNAJ-like domain harbors transforming activity and is involved in DNA replication, which is similar to the *E. coli* DNAJ activity is involved in lambda bacteriophage DNA replication (Campbell et al., 1997).

Figure 11:
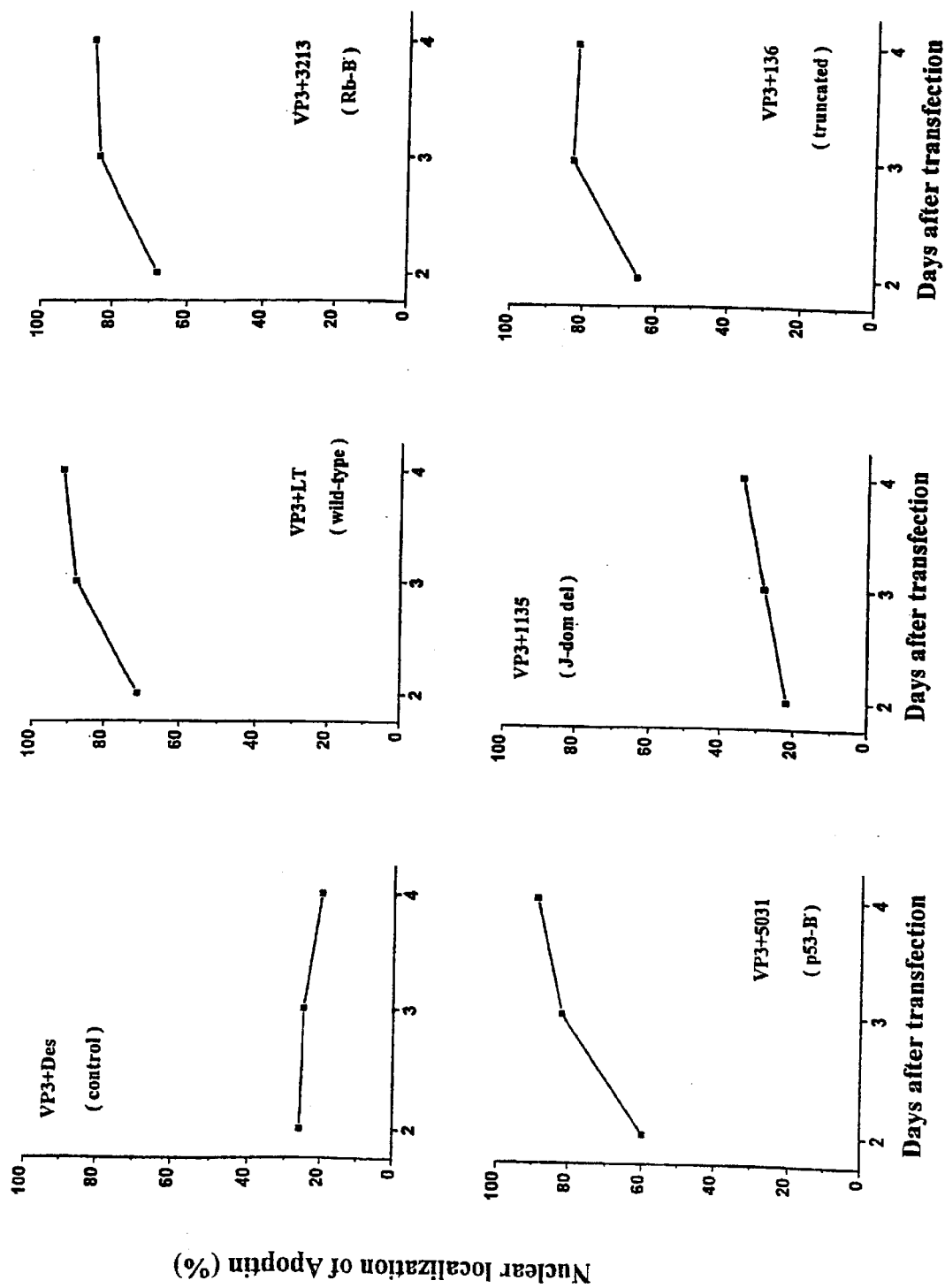
FIG. 11 shows the nuclear localization of Apoptin due to co-expression, as described also for FIG. 10, in normal non-transformed VH10 cells of Apoptin and Desmin (VP3+des; negative control), wild-type SV40 LT (VP3+LT), LT-mutant lacking the retinoblastoma-binding site (VP3+3213), LT-mutant missing the p53-binding sites (VP3+5031), LT-mutant with a deletion in the J domain (VP3+1135), or LT-mutant 136 containing almost only the J domain and a nuclear localization signal (VP3+136). Actually, the % of nuclear localization observed with desmin and Apoptin resembles the background level due to the transfection procedures (Danen-Van Oorschot, 1997).

The LT mutants lacking the Retinoblastoma and p53-binding sites were shown to translocate Apoptin into the nucleus and activate the Apoptin-induced apoptosis to the same extent-as the wild-type LT (Noteborn and Zhang, 1998; FIGS. 10 and 11). These data indicate that both p53 and Retionoblastoma gene products are not relevant for Apoptin-induced apoptosis, which confirms our previous data (Zhang et al., 1995).

In contrast to the LT mutant with the DNAJ-domain deletion, which causes significantly less Apoptin activity in the normal VH10 fibroblasts. This feature shows the importance of the LT DNAJ-like domain on the Apoptin activity. These results are strengthened by the fact that the LT mutant containing almost only the DNAJ-like domain activates Apoptin completely and translocates it optimally into the nucleus (FIGS. 10 and 11).

The SV40 DNAJ-like domain is not homologous to the Apoptin-associating sequences of our newly cloned DNAJ-like cDNA. This observation is in agreement with the fact that Apoptin does not directly associate with the SV40 LT DNAJ-like domain, as detected in co-immunoprecipitations.

Therefore, we conclude that DNAJ-like proteins have at least two independent domains playing a role in Apoptin-induced apoptosis. Nevertheless, these results show the obvious relationship of Apoptin and DNAJ-like activity in the ability of Apoptin induction of apoptosis.

Differential Post-translational Modification Patterns of Apoptin in Transformed/tumorigenic Cells Versus Normal Cells The fact that Apoptin is active in a transformed/tumorigenic cellular background, due to DNAJ-like activities and/or other agents, let us conclude to determine a possible differential modificational characteristic of Apoptin in human transformed/tumorigenic cells versus normal cells.

Therefore, we have carried out a kinase-reaction assay on a bacterial-produced Apoptin protein and lysates obtained from transformed/tumorigenic human cells (Saos-2 cells; Zhuang et al., 1995) or from normal non-transformed VH10 cells. Apoptin incubated with lysate derived from the transformed/tumorigenic human cells was labeled with 32P, whereas Apoptin with lysates derived from normal non-transformed cells was not. These results indicate that (human) transformed/tumorigenic cells harbor an Apoptin-specific kinase activity, which is absent in non-transformed (human) cells.

The fact that Apoptin is differentially post-translationally modified in transformed/tumorigenic versus normal non-transformed cells, forms the base of a diagnostic assay for the determination of transformed/tumorigenic material derived from patients with suspicious tissue.

The advantage of such a method is that one does not need to culture primary (tumor) cells under tissue-culture conditions. Most of the cases, isolated primary (tumor) cells will hardly grow under these conditions.

Production of Polyclonal Antibodies Directed Against DNAJ Like Proteins

For the production of polyclonal antibodies against DNAJ-like proteins a putative immunogenic peptide was synthesized (N-terminus-RNKPVARQAPGKRKC-C/terminus (SEQ ID NO:23); EuroGentec SA, Belgium). Subsequently, rabbits were injected with the specific peptides according to the standard procedures of the manufacturer.

The serum derived from the rabbits injected with the DNAJ-like peptide was shown to be specific for in this report described DNAJ-like products by means of immunofluoresence, and Western-blot assays.

These results imply that we have generated specific antibodies, which can be used for detecting our discovered DNAJ-like Apoptin-associating protein.

REFERENCES

1. Bellamy, C. O. C., Malcomson, R. D. G., Harrison, D. J., and Wyllie, H. 1995. Cell death and disease: The biology and regulation of apoptosis. Seminars in Cancer Biology 6, 3–12.
2. Blatch, G. L., Lassle, M., Zetter, B. R., and Kundra, V. (1997). Isolation of a mouse cDNA encoding mSTI1, a stress-inducible protein containing the TPR motif.
3. Campbell, K. S., Mullane, K. P., Aksoy, I. A., Stubdal, H., Zalvide, J., Pipas, J. M., Silver, P. A., Roberts, P. A., Schaffhausen, B. S., DeCaprio, J. A. (1997). DNAJ/hsp40 chaperone domain of SV40 large T antigen promotes efficient viral DNA replication. Genes an Development 11, 1098–1110
4. Danen-Van Oorschot, A. A. A. M., Fischer, D., Grimbergen, J. M., Klein, B., Zhuang, S.-M., Falkenburg, J. H. F., Backendorf, C., Quax, P. H. A., Van der Eb, J. A., and Noteborn, M. H. M. (1997). Proceedings National Academy Sciences, USA: 94, 5843–5847.
5. Danen-Van Oorschot, A. A. A. M, Den Hollander, A., Takayama, S., Reed, J., Van der Eb, A. J. and Noteborn, M. H. M. (1997a). BAG-1 inhibits p53-induced but not apoptin-induced apoptosis. Apoptosis 2, 395–402.
6. Duke, R. C., Ocjius, D. M., Young, J, D-E. (1996). Cell suicide in health and disease. Scientific American December 1996, 48–55.
7. Durfee, T., Becherer, K., Chen, P.-L., Yeh,S.-H., Yang, Y., Kilburn, A. E., Lee, W.-H., and Elledge, S. J. (1993). The retinoblastoma protein associates with the protein phosphate type I catalytic subunit. Genes and Development 7, 555–569.
8. Earnshaw, W. C., 1995. Nuclear changes in apoptosis. Current Opinion in Cell Biology 7, 337–343.
9. Fields, S. and Song, O. K. (1989). A novel genetic system to detect protein-protein interactions. Nature 340, 245–246.
10. Gazit, G., Kane, S. E., Nichols, P., and Lee, A. S. (1995). Cancer Research 55, 1660–1663.
11. Graham, F. L. and Van der Eb, A. J. (1973). A new technique for the assay of infectivity of human adenovirus 5 DNA. Virology 52, 456–467.
12. Hockenberry, D. M. (1994). Bcl-2 in cancer, development and apoptosis. Journal of Cell Science, Supplement 18, 51–55.
13. Hoffman, C. S. and Winston, F. (1987). A ten-minute DNA preparation from yeast efficiently releases autonomous plasmids for transformation of Escherichia coili. Gene 57, 267–272.
14. Jamora, C., Dennert, G., and Lee, A. S. (196). Inhibition of tumor progression by suppression of stress protein GRP78/BIP induction in fibrosarcoma B/C10ME. Proceedings National Academy Sciences USA 93, 7690–7694.
15. Kerr, J. F. R., Winterford, C. M., and Harmon, B. V. (1994). Apoptosis: Its significance in cancer and cancer therapy. Cancer 73, 2013–2026.

16. Klebe, R. J., Harriss, J. V., Sharp, Z. D., and Douglas, M. G. A general method for polyethylene-glycol-induced genetic transformation of bacteria and yeast. Gene 25, 333–341.
17. Levine, A. J. (1997). p53, the cellular gatekeeper for growth and division. Cell 88, 323–331.
18. Lee, A. S. (1992). Current Opinions of Cell Biology 4, 267–273.
19. Maniatis, T., Fritsch, E. F., and Sambrook, J. (1982). Molecular Cloning: A Laboratory Manual. CSHL Press, New York, USA.
20. Matsudaira, P. (1994). Actin crosslinking proteins at the leading edge. Seminars in Cell Biology 5, 165–174.
21. McDonell T. J., Meyn, R. E., Robertson, L. E. (1995). Implications of apoptotic cell death regulation in cancer therapy. Seminars in Cancer Biology 6, 53–60.
22. Murthy, A. E., Bernards, A., Church, D., Wasmuth, J., and Gusella, J. F. (1996). Identification and characterization of two novel tetratricopeptide repeat-containing genes. DNA and Cell Biology 15, 727–735.
23. Noteborn, M. H. M. (1996). PCT application WO 96/41191. Apoptin induces apoptosis in human transformed and malignant cells but not in normal cells as essential characteristic for the development of an anti-tumor therapy.
24. Noteborn, M. H. M., and De Boer, G. F. (1996). Patent USA/no. 030, 335.
25. Noteborn, M. H. M., De Boer, G. F., Van Roozelaar, D., Karreman, C., Kranenburg, O., Vos, J., Jeurissen, S., Zantema, A., Hoeben, R., Koch, G., Van Ormondt, H., and Van der Eb, A. J. (1991). Characterization of cloned chicken anemia virus DNA that contains all elements for the infectious replication cycle. Journal of Virology 65, 3131–3139.
26. Noteborn, M. H. M., Hoeben, R. C., and Pietersen, A. (1997). A gene delivery vehicle expressing the apoptosis-inducing proteins VP2 and/or apoptin. European Patent Application no. 97201121.7
27. Noteborn, M. H. M., Todd, D., Verschueren, C. A. J., De Gauw, H. W. F. M., Curran, W. L., Veldkamp, S;, Douglas, A. J., McNulty, M. S., Van der Eb, A. J., and Koch, G. (1994). A single chicken anemia virus protein induces apoptosis. Journal of Virology 68, 346–351.
28. Noteborn, M. H. M., and Zhang, Y. (1997). Methods and means for determining the transforming capability of agents, for determining the predisposition of cells to become transformed and prophylactic treatment of cancer using apoptin-like activity. European Patent Application no. 97439
29. Noteborn, M. H. M., Verschueren, C. A. J., Koch, G., and Van der Eb, A. J. (1998). Simultaneous expression of recombinant baculovirus-encoded chicken anemia virus (CAV) proteins VP1 and VP2 is required for formation of the CAV-specific neutralizing epitope. Journal General Virology, in press.
30. Noteborn, M. H. M., and Zhang, Y.-H. (1998). Methods and means for determining the transforming capability of agents, for determining the predisposition of cells to become transformed and prophylactic treatment of cancer using Apoptin-like activity. PCT-application 9720501.9.
31. Paulovich, A. G., Toczyski, D., Hartwell, H. (1997). When checkpoints fail. Cell 88, 315–321.
32. Rose, M. D., Winston, F., and Hieter, P. (1990). Methods in yeast genetics. A laboratory course manual. Cold Spring Harbor Laboratory Press, Cold Spring Harbor, New York, USA
33. Sachs, L. and Lotem, J. (1993). Control of programmed cell death in normal and leukemia cells: New implications for therapy. Blood 82, 15–21.
34. Sanger, F., Nicklen, S., and Coulsen, A. R. (1977). DNA sequencing with chain-terminating inhibitors. Proceedings National Academic Sciences USA 74, 5463–5467.
35. Schlenstedt, G., Harris, S., Risse, B., Lill, R., and Silver, P. A. (1995). A yeast DNAL homologue, Scjlp, can function in the endoplasmic reticulum with Bip/Kar2p via a conserved domain that specifies interactions with Hsp70s.
36. Srinivasan, A., McClellan, A. J., Vartikar, J., Marks, I., Cantalupo, P., Li, Y., Whyte, P., Rundell, K., Brodsky, J. L., and Pipas, J. M. (1997). The amino-terminal transforming region of simian virus 40 large T and small t antihgens functions as a J domain. Molecular and Cellular Biology 17, 4761–4773.
37. Steller, H. (1995). Mechanisms and genes of cellular suicide. Science 267, 1445–1449.
38. Sugawara, S., Takeda, K., Lee, A., and Dennert, G. (1993). Cancer Research 53, 6001–6005.
39. Telford, W. G., King, L. E., Fraker, P. J. (1992). Comparative evaluation of several DNA binding dyes in the detection of apoptosis-associated chromatin degradation by flow cytometry. Cytometry 13, 137–143.
40. Teodoro, J. G. and Branton, P. E. (1997). Regulation of apoptosis by viral gene products. Journal of Virology 71, 1739–1746.
41. Thompson, C. B. (1995). Apoptosis in the pathogenesis and treatment of disease. Science 267, 1456–1462.
42. White, E. (1996). Life, death, and the pursuit of apoptosis. Genes and development 10, 1–15.
43. Wyllie, A. H. (1995). The genetic regulation of apoptosis. Current Opinion in Genetics and Development 5, 97–104.
44. Wyllie, A. H., Kerr, J. F. R., Currie, A. R. (1980). Cell death: The significance of apoptosis. International Review of Cytology 68, 251–306.
45. Yang, X., Hubbard, E. J. A., and Carlson, M. (1992). A protein kinase substrate identified by the two-hybrid system. Science 257, 680–682.
46. Zhuang, S.-M., Landegent, J. E., Verschueren, C. A. J., Falkenburg, J. H. F., Van Ormondt, H., Van der Eb, A. J., Noteborn, M. H. M. (1995). Apoptin, a protein encoded by chicken anemia virus, induces cell death in various human hematologic malignant cells in vitro. Leukemia 9 S1, 118–120.
47. Zhuang, S.-M., Shvarts, A., Van Ormondt, H., Jochemsen, A.-G., Van der Eb, A. J., Noteborn, M. H. M. (1995). Apoptin, a protein de rived from chicken anemia virus, induces a p53-independent apoptosis in human osteosarcoma cells. Cancer Research 55, 486–489.

What is claimed is:

1. A method for inducing apoptosis in a cell that expresses Bip/GRP78, said method comprising:
   providing said cell with apoptin which interferes with Bip/GRP78-mediated apoptosis inhibiting activity.

2. A method for inducing apoptosis in a cell, said method comprising:
   providing said cell with apoptin and a second protein wherein said second protein comprises Bip/GRP78-mediated apoptosis inhibiting activity and wherein said second protein associates with apoptin.

3. The method according to claim 2, wherein said apoptin and said second protein are provided by expression of nucleic acid molecules encoding said apoption and said second protein.

4. The method according to claim 1, wherein said interfering is provided by Bip/GRP78 associating with said apoptin protein.

5. The method according to claim 2, wherein when said second protein associates with apoptin, said apoptin is translocated to the nucleus of said cell.

6. The method according to claim 2, wherein apoptosis induction is enhanced by further providing said cell with VP2.

* * * * *

UNITED STATES PATENT AND TRADEMARK OFFICE
CERTIFICATE OF CORRECTION

PATENT NO. : 6,472,142 B1  Page 1 of 1
DATED : October 29, 2002
INVENTOR(S) : Noteborn et al.

It is certified that error appears in the above-identified patent and that said Letters Patent is hereby corrected as shown below:

Title page,
Item [56], References Cited, change "Noteborn, et al., J. of Virology (1991), 65:313-9" to -- Noteborn, et al., J. of Virology (1991), 65:3131-9 --

Column 4,
Line 3, change "NO:13-)." to -- NO:13-14). --

Column 5,
Line 6, change "prurified" to -- purified --
Line 48, change "0,246" to -- 0.246 --

Column 10,
Line 65, change "pS53-binding" to -- p53-binding --

Column 12,
Line 58, change "coili" to -- coli --

Column 14,
Line 20, change "antihgens" to -- antigens --
Line 54, change "de rived" to -- derived --

Signed and Sealed this

Fourth Day of March, 2003

JAMES E. ROGAN
*Director of the United States Patent and Trademark Office*

SEQUENCE LISTING

<160> NUMBER OF SEQ ID NOS: 23

<210> SEQ ID NO 1
<211> LENGTH: 661
<212> TYPE: DNA
<213> ORGANISM: Homo sapiens
<220> FEATURE:
<221> NAME/KEY: misc_feature
<222> LOCATION: (91)..(91)
<223> OTHER INFORMATION: The "n" at position 91 may be any of g, a, t
      or c.
<220> FEATURE:
<221> NAME/KEY: misc_feature
<222> LOCATION: (186)..(186)
<223> OTHER INFORMATION: The "n" at position 186 may be any of g, a,
      t or c.
<220> FEATURE:
<221> NAME/KEY: misc_feature
<222> LOCATION: (206)..(206)
<223> OTHER INFORMATION: The "n" at position 206 may be any of g, a,
      t or c.
<220> FEATURE:
<221> NAME/KEY: misc_feature
<222> LOCATION: (259)..(259)
<223> OTHER INFORMATION: The "n" at position 259 may be any of g, a,
      t or c.
<220> FEATURE:
<221> NAME/KEY: misc_feature
<222> LOCATION: (265)..(265)
<223> OTHER INFORMATION: The "n" at position 265 may be any of g, a,
      t or c.
<220> FEATURE:
<221> NAME/KEY: misc_feature
<222> LOCATION: (306)..(306)
<223> OTHER INFORMATION: The "n" at position 306 may be any of g, a,
      t or c.
<220> FEATURE:
<221> NAME/KEY: misc_feature
<222> LOCATION: (315)..(315)
<223> OTHER INFORMATION: The "n" at position 315 may be any of g, a,
      t or c.
<220> FEATURE:
<221> NAME/KEY: misc_feature
<222> LOCATION: (336)..(336)
<223> OTHER INFORMATION: The "n" at position 336 may be any of g, a,
      t or c.
<220> FEATURE:
<221> NAME/KEY: misc_feature
<222> LOCATION: (344)..(344)
<223> OTHER INFORMATION: The "n" at position 344 may be any of g, a,
      t or c.
<220> FEATURE:
<221> NAME/KEY: misc_feature
<222> LOCATION: (352)..(352)
<223> OTHER INFORMATION: The "n" at position 352 may be any of g, a,
      t or c.
<220> FEATURE:
<221> NAME/KEY: misc_feature
<222> LOCATION: (375)..(375)
<223> OTHER INFORMATION: The "n" at position 375 may be any of g, a,
      t or c.
<220> FEATURE:
<221> NAME/KEY: misc_feature
<222> LOCATION: (381)..(381)
<223> OTHER INFORMATION: The "n" at position 381 may be any of g, a,
      t or c.
<220> FEATURE:
<221> NAME/KEY: misc_feature
<222> LOCATION: (387)..(387)
<223> OTHER INFORMATION: The "n" at position 387 may be any of g, a,
      t or c.
<220> FEATURE:
<221> NAME/KEY: misc_feature
<222> LOCATION: (412)..(412)
<223> OTHER INFORMATION: The "n" at position 412 may be any of g, a,
      t or c.

-continued

```
<220> FEATURE:
<221> NAME/KEY: misc_feature
<222> LOCATION: (416)..(416)
<223> OTHER INFORMATION: The "n" at position 416 may be any of g, a,
      t or c.
<220> FEATURE:
<221> NAME/KEY: misc_feature
<222> LOCATION: (420)..(420)
<223> OTHER INFORMATION: The "n" at position 420 may be any of g, a,
      t or c.
<220> FEATURE:
<221> NAME/KEY: misc_feature
<222> LOCATION: (434)..(434)
<223> OTHER INFORMATION: The "n" at position 434 may be any of g, a,
      t or c.
<220> FEATURE:
<221> NAME/KEY: misc_feature
<222> LOCATION: (438)..(439)
<223> OTHER INFORMATION: The "n" at positions 438-39 may be any of g,
      a, t or c.
<220> FEATURE:
<221> NAME/KEY: misc_feature
<222> LOCATION: (452)..(452)
<223> OTHER INFORMATION: The "n" at position 452 may be any of g, a,
      t or c.
<220> FEATURE:
<221> NAME/KEY: misc_feature
<222> LOCATION: (455)..(455)
<223> OTHER INFORMATION: The "n" at position 455 may be any of g, a,
      t or c.
<220> FEATURE:
<221> NAME/KEY: misc_feature
<222> LOCATION: (459)..(459)
<223> OTHER INFORMATION: The "n" at position 459 may be any of g, a,
      t or c.
<220> FEATURE:
<221> NAME/KEY: misc_feature
<222> LOCATION: (467)..(467)
<223> OTHER INFORMATION: The "n" at position 467 may be any of g, a,
      t or c.
<220> FEATURE:
<221> NAME/KEY: misc_feature
<222> LOCATION: (480)..(480)
<223> OTHER INFORMATION: The "n" at position 480 may be any of g, a,
      t or c.
<220> FEATURE:
<221> NAME/KEY: misc_feature
<222> LOCATION: (486)..(487)
<223> OTHER INFORMATION: The "n" at positions 486-87 may be any of g,
      a, t or c.
<220> FEATURE:
<221> NAME/KEY: misc_feature
<222> LOCATION: (491)..(491)
<223> OTHER INFORMATION: The "n" at position 491 may be any of g, a,
      t or c.
<220> FEATURE:
<221> NAME/KEY: misc_feature
<222> LOCATION: (497)..(497)
<223> OTHER INFORMATION: The "n" at position 497 may be any of g, a,
      t or c.
<220> FEATURE:
<221> NAME/KEY: misc_feature
<222> LOCATION: (499)..(499)
<223> OTHER INFORMATION: The "n" at position 499 may be any of g, a,
      t or c.
<220> FEATURE:
<221> NAME/KEY: misc_feature
<222> LOCATION: (505)..(506)
<223> OTHER INFORMATION: The "n" at positions 505-506 may be any of g,
      a, t or c.
<220> FEATURE:
<221> NAME/KEY: misc_feature
<222> LOCATION: (513)..(513)
<223> OTHER INFORMATION: The "n" at position 513 may be any of g, a,
      t or c.
<220> FEATURE:
<221> NAME/KEY: misc_feature
<222> LOCATION: (520)..(520)
<223> OTHER INFORMATION: The "n" at position 520 may be any of g, a,
```

-continued

```
       t or c.
<220>  FEATURE:
<221>  NAME/KEY: misc_feature
<222>  LOCATION: (538)..(538)
<223>  OTHER INFORMATION: The "n" at position 538 may be any of g, a,
       t or c.
<220>  FEATURE:
<221>  NAME/KEY: misc_feature
<222>  LOCATION: (540)..(540)
<223>  OTHER INFORMATION: The "n" at position 540 may be any of g, a,
       t or c.
<220>  FEATURE:
<221>  NAME/KEY: misc_feature
<222>  LOCATION: (543)..(543)
<223>  OTHER INFORMATION: The "n" at position 543 may be any of g, a,
       t or c.
<220>  FEATURE:
<221>  NAME/KEY: misc_feature
<222>  LOCATION: (545)..(545)
<223>  OTHER INFORMATION: The "n" at position 545 may be any of g, a,
       t or c.
<220>  FEATURE:
<221>  NAME/KEY: misc_feature
<222>  LOCATION: (552)..(552)
<223>  OTHER INFORMATION: The "n" at position 552 may be any of g, a,
       t or c.
<220>  FEATURE:
<221>  NAME/KEY: misc_feature
<222>  LOCATION: (554)..(554)
<223>  OTHER INFORMATION: The "n" at position 554 may be any of g, a,
       t or c.
<220>  FEATURE:
<221>  NAME/KEY: misc_feature
<222>  LOCATION: (556)..(556)
<223>  OTHER INFORMATION: The "n" at position 556 may be any of g, a,
       t or c.
<220>  FEATURE:
<221>  NAME/KEY: misc_feature
<222>  LOCATION: (559)..(560)
<223>  OTHER INFORMATION: The "n" at positions 559-560 may be any of g,
       a, t or c.
<220>  FEATURE:
<221>  NAME/KEY: misc_feature
<222>  LOCATION: (578)..(578)
<223>  OTHER INFORMATION: The "n" at position 578 may be any of g, a,
       t or c.
<220>  FEATURE:
<221>  NAME/KEY: misc_feature
<222>  LOCATION: (583)..(583)
<223>  OTHER INFORMATION: The "n" at position 583 may be any of g, a,
       t or c.
<220>  FEATURE:
<221>  NAME/KEY: misc_feature
<222>  LOCATION: (597)..(597)
<223>  OTHER INFORMATION: The "n" at position 597 may be any of g, a,
       t or c.
<220>  FEATURE:
<221>  NAME/KEY: misc_feature
<222>  LOCATION: (600)..(600)
<223>  OTHER INFORMATION: The "n" at position 600 may be any of g, a,
       t or c.
<220>  FEATURE:
<221>  NAME/KEY: misc_feature
<222>  LOCATION: (605)..(605)
<223>  OTHER INFORMATION: The "n" at position 605 may be any of g, a,
       t or c.
<220>  FEATURE:
<221>  NAME/KEY: misc_feature
<222>  LOCATION: (611)..(611)
<223>  OTHER INFORMATION: The "n" at position 611 may be any of g, a,
       t or c.
<220>  FEATURE:
<221>  NAME/KEY: misc_feature
<222>  LOCATION: (616)..(616)
<223>  OTHER INFORMATION: The "n" at position 616 may be any of g, a,
       t or c.
<220>  FEATURE:
<221>  NAME/KEY: misc_feature
<222>  LOCATION: (624)..(624)
```

```
<223> OTHER INFORMATION: The "n" at position 624 may be any of g, a,
      t or c.
<220> FEATURE:
<221> NAME/KEY: misc_feature
<222> LOCATION: (627)..(629)
<223> OTHER INFORMATION: The "n" at positions 627-629 may be any of g,
      a, t or c.
<220> FEATURE:
<221> NAME/KEY: misc_feature
<222> LOCATION: (631)..(631)
<223> OTHER INFORMATION: The "n" at position 631 may be any of g, a,
      t or c.
<220> FEATURE:
<221> NAME/KEY: misc_feature
<222> LOCATION: (634)..(634)
<223> OTHER INFORMATION: The "n" at position 634 may be any of g, a,
      t or c.
<220> FEATURE:
<221> NAME/KEY: misc_feature
<222> LOCATION: (639)..(640)
<223> OTHER INFORMATION: The "n" at positions 639-640 may be any of g,
      a, t or c.
<220> FEATURE:
<221> NAME/KEY: misc_feature
<222> LOCATION: (650)..(650)
<223> OTHER INFORMATION: The "n" at position 650 may be any of g, a,
      t or c.
<220> FEATURE:
<221> NAME/KEY: misc_feature
<222> LOCATION: (659)..(659)
<223> OTHER INFORMATION: The "n" at position 659 may be any of g, a,
      t or c.

<400> SEQUENCE: 1
cagcttctga taatcaacca actgttacaa tcaaggtcta tgaaggtgaa agacccctga     60
caaaagacaa tcatcttctg ggtacatttg ntccgactgg aattcctcct gctcctcgtg    120
gggtcccaca gattgaagtc acctttgaga tagatgtgaa tggtattctt cgaagtgaca    180
gctgangaca agggtacagg gaacanaaat aagatcacaa tcaccaatga ccagaatcgc    240
ctgacacctg aagaaatcna aggntggtt aatgatgctg agaattttgc tgaggaagac     300
aaaaanctca aggancgcat tgatactaga atgganttgg aaanctatgc cnattctcta    360
aagaatcaga ttggngataa ngaaaanctg gaaggtaaac tttcctcgga anatanggan    420
accatggaaa aacntgtnna agaaaaaatt tngantggnt ggaaaancaa ccaatatgcn    480
gacttnnaaa nttcaangnt aagannaggg aantgggaan aattttttcac ccatttttncn   540 agnanaccct angnanttnn aaggccccccc cccaattngg tanagggtt ccaccanaan    600 aaatngtttt ntcacncggt ttcngannng nctnttaann ttgtaaaatn ggggcccccnt   660 t                                                                    661

<210> SEQ ID NO 2
<211> LENGTH: 622
<212> TYPE: DNA
<213> ORGANISM: Homo sapiens
<220> FEATURE:
<221> NAME/KEY: misc_feature
<222> LOCATION: (484)..(484)
<223> OTHER INFORMATION: The "n" at position 484 may be any of g, a,
      t or c.
<220> FEATURE:
<221> NAME/KEY: misc_feature
<222> LOCATION: (500)..(500)
<223> OTHER INFORMATION: The "n" at position 500 may be any of g, a,
      t or c.
<220> FEATURE:
<221> NAME/KEY: misc_feature
<222> LOCATION: (503)..(503)
<223> OTHER INFORMATION: The "n" at position 503 may be any of g, a,
      t or c.
```

```
<220> FEATURE:
<221> NAME/KEY: misc_feature
<222> LOCATION: (515)..(515)
<223> OTHER INFORMATION: The "n" at position 515 may be any of g, a,
      t or c.
<220> FEATURE:
<221> NAME/KEY: misc_feature
<222> LOCATION: (517)..(517)
<223> OTHER INFORMATION: The "n" at position 517 may be any of g, a,
      t or c.
<220> FEATURE:
<221> NAME/KEY: misc_feature
<222> LOCATION: (528)..(528)
<223> OTHER INFORMATION: The "n" at position 528 may be any of g, a,
      t or c.
<220> FEATURE:
<221> NAME/KEY: misc_feature
<222> LOCATION: (583)..(583)
<223> OTHER INFORMATION: The "n" at position 583 may be any of g, a,
      t or c.
<220> FEATURE:
<221> NAME/KEY: misc_feature
<222> LOCATION: (591)..(591)
<223> OTHER INFORMATION: The "n" at position 591 may be any of g, a,
      t or c.
<220> FEATURE:
<221> NAME/KEY: misc_feature
<222> LOCATION: (594)..(594)
<223> OTHER INFORMATION: The "n" at position 594 may be any of g, a,
      t or c.

<400> SEQUENCE: 2
cagcttctga taatcaacca actgttacaa tcaaggtcta tgaaggtgaa agacccctga      60
caaaagacaa tcatcttctg ggtacatttg atctgactgg aattcctcct gctcctcgtg     120
gggtcccaca gattgaagtc acctttgaga tagatgtgaa tggtattctt cgagtgacag     180
ctgaagacaa gggtacaggg aacaaaaata agatcacaat caccaatgac cagaatcgcc     240
tgacacctga agaaatcgaa aggatggtta atgatgctga aagtttgct gaggaagaca      300 aaaagctcaa ggagcgcatt gatactagaa atgagttgga aagctatgcc tattctctaa     360
agaatcagat tggagataaa gaaaagctgg gaggtaaaact ttcctctgaa gataaggaga    420
ccatggaaaa agctgtagaa gaaaagattg aatggctgga aagccaccaa gatgctgaca     480
ttgnagactt caaagctaan aangaaggaa ctggnanaaa ttgttcancc aattatcagc     540
aaactccaat ggaagtgcaa gccctccccc aactggtgaa gangatacaa ncangaaaaa     600
gatgagttgt tacactgatc tt                                              622

<210> SEQ ID NO 3
<211> LENGTH: 703
<212> TYPE: DNA
<213> ORGANISM: Homo sapiens
<220> FEATURE:
<221> NAME/KEY: misc_feature
<222> LOCATION: (55)..(55)
<223> OTHER INFORMATION: The "n" at position 55 may be any of g, a,
      t or c.
<220> FEATURE:
<221> NAME/KEY: misc_feature
<222> LOCATION: (100)..(100)
<223> OTHER INFORMATION: The "n" at position 100 may be any of g, a,
      t or c.
<220> FEATURE:
<221> NAME/KEY: misc_feature
<222> LOCATION: (132)..(132)
<223> OTHER INFORMATION: The "n" at position 132 may be any of g, a,
      t or c.
<220> FEATURE:
<221> NAME/KEY: misc_feature
<222> LOCATION: (175)..(177)
<223> OTHER INFORMATION: The "n" at positions 175-177 may be any of
```

```
        g, a, t or c.
<220> FEATURE:
<221> NAME/KEY: misc_feature
<222> LOCATION: (181)..(181)
<223> OTHER INFORMATION: The "n" at position 181 may be any of g, a,
        t or c.
<220> FEATURE:
<221> NAME/KEY: misc_feature
<222> LOCATION: (200)..(200)
<223> OTHER INFORMATION: The "n" at position 200 may be any of g, a,
        t or c.
<220> FEATURE:
<221> NAME/KEY: misc_feature
<222> LOCATION: (214)..(214)
<223> OTHER INFORMATION: The "n" at position 214 may be any of g, a,
        t or c.
<220> FEATURE:
<221> NAME/KEY: misc_feature
<222> LOCATION: (216)..(216)
<223> OTHER INFORMATION: The "n" at position 216 may be any of g, a,
        t or c.
<220> FEATURE:
<221> NAME/KEY: misc_feature
<222> LOCATION: (232)..(232)
<223> OTHER INFORMATION: The "n" at position 232 may be any of g, a,
        t or c.
<220> FEATURE:
<221> NAME/KEY: misc_feature
<222> LOCATION: (238)..(238)
<223> OTHER INFORMATION: The "n" at position 238 may be any of g, a,
        t or c.
<220> FEATURE:
<221> NAME/KEY: misc_feature
<222> LOCATION: (243)..(243)
<223> OTHER INFORMATION: The "n" at position 243 may be any of g, a,
        t or c.
<220> FEATURE:
<221> NAME/KEY: misc_feature
<222> LOCATION: (250)..(250)
<223> OTHER INFORMATION: The "n" at position 250 may be any of g, a,
        t or c.
<220> FEATURE:
<221> NAME/KEY: misc_feature
<222> LOCATION: (256)..(256)
<223> OTHER INFORMATION: The "n" at position 256 may be any of g, a,
        t or c.
<220> FEATURE:
<221> NAME/KEY: misc_feature
<222> LOCATION: (280)..(280)
<223> OTHER INFORMATION: The "n" at position 280 may be any of g, a,
        t or c.
<220> FEATURE:
<221> NAME/KEY: misc_feature
<222> LOCATION: (297)..(297)
<223> OTHER INFORMATION: The "n" at position 297 may be any of g, a,
        t or c.
<220> FEATURE:
<221> NAME/KEY: misc_feature
<222> LOCATION: (301)..(301)
<223> OTHER INFORMATION: The "n" at position 301 may be any of g, a,
        t or c.
<220> FEATURE:
<221> NAME/KEY: misc_feature
<222> LOCATION: (317)..(317)
<223> OTHER INFORMATION: The "n" at position 317 may be any of g, a,
        t or c.
<220> FEATURE:
<221> NAME/KEY: misc_feature
<222> LOCATION: (338)..(338)
<223> OTHER INFORMATION: The "n" at position 338 may be any of g, a,
        t or c.
<220> FEATURE:
<221> NAME/KEY: misc_feature
<222> LOCATION: (374)..(374)
<223> OTHER INFORMATION: The "n" at position 374 may be any of g, a,
        t or c.
<220> FEATURE:
<221> NAME/KEY: misc_feature
<222> LOCATION: (378)..(378)
```

```
<223> OTHER INFORMATION: The "n" at position 378 may be any of g, a,
      t or c.
<220> FEATURE:
<221> NAME/KEY: misc_feature
<222> LOCATION: (385)..(385)
<223> OTHER INFORMATION: The "n" at position 385 may be any of g, a,
      t or c.
<220> FEATURE:
<221> NAME/KEY: misc_feature
<222> LOCATION: (397)..(397)
<223> OTHER INFORMATION: The "n" at position 397 may be any of g, a,
      t or c.
<220> FEATURE:
<221> NAME/KEY: misc_feature
<222> LOCATION: (400)..(400)
<223> OTHER INFORMATION: The "n" at position 400 may be any of g, a,
      t or c.
<220> FEATURE:
<221> NAME/KEY: misc_feature
<222> LOCATION: (407)..(407)
<223> OTHER INFORMATION: The "n" at position 407 may be any of g, a,
      t or c.
<220> FEATURE:
<221> NAME/KEY: misc_feature
<222> LOCATION: (415)..(415)
<223> OTHER INFORMATION: The "n" at position 415 may be any of g, a,
      t or c.
<220> FEATURE:
<221> NAME/KEY: misc_feature
<222> LOCATION: (420)..(421)
<223> OTHER INFORMATION: The "n" at positions 420-421 may be any of g,
      a, t or c.
<220> FEATURE:
<221> NAME/KEY: misc_feature
<222> LOCATION: (423)..(424)
<223> OTHER INFORMATION: The "n" at positions 423-424 may be any of g,
      a, t or c.
<220> FEATURE:
<221> NAME/KEY: misc_feature
<222> LOCATION: (427)..(427)
<223> OTHER INFORMATION: The "n" at position 427 may be any of g, a,
      t or c.
<220> FEATURE:
<221> NAME/KEY: misc_feature
<222> LOCATION: (431)..(431)
<223> OTHER INFORMATION: The "n" at position 431 may be any of g, a,
      t or c.
<220> FEATURE:
<221> NAME/KEY: misc_feature
<222> LOCATION: (441)..(441)
<223> OTHER INFORMATION: The "n" at position 441 may be any of g, a,
      t or c.
<220> FEATURE:
<221> NAME/KEY: misc_feature
<222> LOCATION: (443)..(443)
<223> OTHER INFORMATION: The "n" at position 443 may be any of g, a,
      t or c.
<220> FEATURE:
<221> NAME/KEY: misc_feature
<222> LOCATION: (445)..(445)
<223> OTHER INFORMATION: The "n" at position 445 may be any of g, a,
      t or c.
<220> FEATURE:
<221> NAME/KEY: misc_feature
<222> LOCATION: (449)..(449)
<223> OTHER INFORMATION: The "n" at position 449 may be any of g, a,
      t or c.
<220> FEATURE:
<221> NAME/KEY: misc_feature
<222> LOCATION: (456)..(456)
<223> OTHER INFORMATION: The "n" at position 456 may be any of g, a,
      t or c.
<220> FEATURE:
<221> NAME/KEY: misc_feature
<222> LOCATION: (459)..(459)
<223> OTHER INFORMATION: The "n" at position 459 may be any of g, a,
      t or c.
<220> FEATURE:
<221> NAME/KEY: misc_feature
```

```
<222> LOCATION: (469)..(469)
<223> OTHER INFORMATION: The "n" at position 469 may be any of g, a,
      t or c.
<220> FEATURE:
<221> NAME/KEY: misc_feature
<222> LOCATION: (473)..(474)
<223> OTHER INFORMATION: The "n" at positions 473-474 may be any of
      g, a, t or c.
<220> FEATURE:
<221> NAME/KEY: misc_feature
<222> LOCATION: (480)..(480)
<223> OTHER INFORMATION: The "n" at position 480 may be any of g, a,
      t or c.
<220> FEATURE:
<221> NAME/KEY: misc_feature
<222> LOCATION: (494)..(494)
<223> OTHER INFORMATION: The "n" at position 494 may be any of g, a,
      t or c.
<220> FEATURE:
<221> NAME/KEY: misc_feature
<222> LOCATION: (503)..(503)
<223> OTHER INFORMATION: The "n" at position 503 may be any of g, a,
      t or c.
<220> FEATURE:
<221> NAME/KEY: misc_feature
<222> LOCATION: (514)..(516)
<223> OTHER INFORMATION: The "n" at positions 514-516 may be any of
      g, a, t or c.
<220> FEATURE:
<221> NAME/KEY: misc_feature
<222> LOCATION: (518)..(518)
<223> OTHER INFORMATION: The "n" at position 518 may be any of g, a,
      t or c.
<220> FEATURE:
<221> NAME/KEY: misc_feature
<222> LOCATION: (522)..(522)
<223> OTHER INFORMATION: The "n" at position 522 may be any of g, a,
      t or c.
<220> FEATURE:
<221> NAME/KEY: misc_feature
<222> LOCATION: (538)..(538)
<223> OTHER INFORMATION: The "n" at position 538 may be any of g, a,
      t or c.
<220> FEATURE:
<221> NAME/KEY: misc_feature
<222> LOCATION: (540)..(540)
<223> OTHER INFORMATION: The "n" at position 540 may be any of g, a,
      t or c.
<220> FEATURE:
<221> NAME/KEY: misc_feature
<222> LOCATION: (546)..(546)
<223> OTHER INFORMATION: The "n" at position 546 may be any of g, a,
      t or c.
<220> FEATURE:
<221> NAME/KEY: misc_feature
<222> LOCATION: (550)..(551)
<223> OTHER INFORMATION: The "n" at positions 550-551 may be any of
      g, a, t or c.
<220> FEATURE:
<221> NAME/KEY: misc_feature
<222> LOCATION: (561)..(561)
<223> OTHER INFORMATION: The "n" at position 561 may be any of g,
      a, t or c.
<220> FEATURE:
<221> NAME/KEY: misc_feature
<222> LOCATION: (566)..(566)
<223> OTHER INFORMATION: The "n" at position 566 may be any of g,
      a, t or c.
<220> FEATURE:
<221> NAME/KEY: misc_feature
<222> LOCATION: (570)..(570)
<223> OTHER INFORMATION: The "n" at position 570 may be any of g,
      a, t or c.
<220> FEATURE:
<221> NAME/KEY: misc_feature
<222> LOCATION: (575)..(575)
<223> OTHER INFORMATION: The "n" at position 575 may be any of g,
      a, t or c.
<220> FEATURE:
```

-continued

```
<221> NAME/KEY: misc_feature
<222> LOCATION: (579)..(579)
<223> OTHER INFORMATION: The "n" at position 579 may be any of g,
      a, t or c.
<220> FEATURE:
<221> NAME/KEY: misc_feature
<222> LOCATION: (582)..(582)
<223> OTHER INFORMATION: The "n" at position 582 may be any of g,
      a, t or c.
<220> FEATURE:
<221> NAME/KEY: misc_feature
<222> LOCATION: (585)..(586)
<223> OTHER INFORMATION: The "n" at positions 585-586 may be any of
      g, a, t or c.
<220> FEATURE:
<221> NAME/KEY: misc_feature
<222> LOCATION: (589)..(589)
<223> OTHER INFORMATION: The "n" at position 589 may be any of g,
      a, t or c.
<220> FEATURE:
<221> NAME/KEY: misc_feature
<222> LOCATION: (594)..(595)
<223> OTHER INFORMATION: The "n" at positions 594-595 may be any of
      g, a, t or c.
<220> FEATURE:
<221> NAME/KEY: misc_feature
<222> LOCATION: (606)..(606)
<223> OTHER INFORMATION: The "n" at position 606 may be any of g,
      a, t or c.
<220> FEATURE:
<221> NAME/KEY: misc_feature
<222> LOCATION: (608)..(608)
<223> OTHER INFORMATION: The "n" at position 608 may be any of g,
      a, t or c.
<220> FEATURE:
<221> NAME/KEY: misc_feature
<222> LOCATION: (617)..(617)
<223> OTHER INFORMATION: The "n" at position 617 may be any of g,
      a, t or c.
<220> FEATURE:
<221> NAME/KEY: misc_feature
<222> LOCATION: (623)..(623)
<223> OTHER INFORMATION: The "n" at position 623 may be any of g,
      a, t or c.
<220> FEATURE:
<221> NAME/KEY: misc_feature
<222> LOCATION: (627)..(627)
<223> OTHER INFORMATION: The "n" at position 627 may be any of g,
      a, t or c.
<220> FEATURE:
<221> NAME/KEY: misc_feature
<222> LOCATION: (639)..(639)
<223> OTHER INFORMATION: The "n" at position 639 may be any of g,
      a, t or c.
<220> FEATURE:
<221> NAME/KEY: misc_feature
<222> LOCATION: (643)..(644)
<223> OTHER INFORMATION: The "n" at positions 643-644 may be any of
      g, a, t or c.
<220> FEATURE:
<221> NAME/KEY: misc_feature
<222> LOCATION: (647)..(647)
<223> OTHER INFORMATION: The "n" at position 647 may be any of g, a,
      t or c.
<220> FEATURE:
<221> NAME/KEY: misc_feature
<222> LOCATION: (656)..(656)
<223> OTHER INFORMATION: The "n" at position 656 may be any of g, a,
      t or c.
<220> FEATURE:
<221> NAME/KEY: misc_feature
<222> LOCATION: (659)..(659)
<223> OTHER INFORMATION: The "n" at position 659 may be any of g, a,
      t or c.
<220> FEATURE:
<221> NAME/KEY: misc_feature
<222> LOCATION: (663)..(663)
<223> OTHER INFORMATION: The "n" at position 663 may be any of g, a,
      t or c.
```

```
<220> FEATURE:
<221> NAME/KEY: misc_feature
<222> LOCATION: (669)..(669)
<223> OTHER INFORMATION: The "n" at position 669 may be any of g, a,
      t or c.
<220> FEATURE:
<221> NAME/KEY: misc_feature
<222> LOCATION: (672)..(672)
<223> OTHER INFORMATION: The "n" at position 672 may be any of g, a,
      t or c.
<220> FEATURE:
<221> NAME/KEY: misc_feature
<222> LOCATION: (677)..(677)
<223> OTHER INFORMATION: The "n" at position 677 may be any of g, a,
      t or c.
<220> FEATURE:
<221> NAME/KEY: misc_feature
<222> LOCATION: (680)..(680)
<223> OTHER INFORMATION: The "n" at position 680 may be any of g, a,
      t or c.
<220> FEATURE:
<221> NAME/KEY: misc_feature
<222> LOCATION: (686)..(686)
<223> OTHER INFORMATION: The "n" at position 686 may be any of g, a,
      t or c.
<220> FEATURE:
<221> NAME/KEY: misc_feature
<222> LOCATION: (688)..(688)
<223> OTHER INFORMATION: The "n" at position 688 may be any of g, a,
      t or c.
<220> FEATURE:
<221> NAME/KEY: misc_feature
<222> LOCATION: (694)..(694)
<223> OTHER INFORMATION: The "n" at position 694 may be any of g, a,
      t or c.

<400> SEQUENCE: 3
ctgataatca accaactgtt acaatcaagg tctatgaagg tgaaagaccc ctganaaaag      60
acaatcatct tctgggtaca tttgatttga caaacattcn tcctgctcct cgtggggtcc    120
cacagattga tngtcacctt tgagatagat gtgaatggta ttcttcgagt gacannntga    180
ncgacaaggg tacagggaan aaaactaaga tcanantcac caaatgatca anaatcgnct    240
ganacctgan gaaatngaaa ggatggttaa tgatgctgan gaagtttgct gaggaanaca    300
naaagctcaa ggagcgnatt gatattagaa gtgagttnga aagctatgcc tattctctat    360
agaatcagat tggngatnat tgaanagctg ggaggtnaan ttcctcngat agatnaggan    420
nannatngaa ngaagctgta ntngnaaang attganatng gctggaaang ctnncaaagn    480
atgcttaaca ttgnaaggac ttnaatagct taannnanaa gngtactggg tataaaantn    540
gttcanccan nttatcatca ngtttncatn ggaangtgna anggnnctnc tcgnnaactg    600
ggtgantnag gtttcancaa ganaaantat taagtttgnt agnnacngga tctggntang    660
tgnctgtana antggtntan tacggngnct caanggaact tag                      703

<210> SEQ ID NO 4
<211> LENGTH: 618
<212> TYPE: DNA
<213> ORGANISM: Homo sapiens
<220> FEATURE:
<221> NAME/KEY: misc_feature
<222> LOCATION: (362)..(362)
<223> OTHER INFORMATION: The "n" at position 362 may be any of g, a,
      t, or c.
<220> FEATURE:
<221> NAME/KEY: misc_feature
<222> LOCATION: (426)..(426)
<223> OTHER INFORMATION: The "n" at position 426 may be any of g, a,
      t, or c.
<220> FEATURE:
<221> NAME/KEY: misc_feature
```

```
<222> LOCATION: (433)..(433)
<223> OTHER INFORMATION: The "n" at position 433 may be any of g, a,
      t, or c.
<220> FEATURE:
<221> NAME/KEY: misc_feature
<222> LOCATION: (605)..(605)
<223> OTHER INFORMATION: The "n" at position 605 may be any of g, a,
      t, or c.
<220> FEATURE:
<221> NAME/KEY: misc_feature
<222> LOCATION: (608)..(608)
<223> OTHER INFORMATION: The "n" at position 608 may be any of g, a,
      t, or c.

<400> SEQUENCE: 4
ggccacgaag gcccacagtg gtgcctacca agaagtctca gatcttttct acagcttctg      60
ataatcaacc aactgttaca atcaaggtct atgaaggtga agaccctg acaaaagaca      120 atcatcttct gggtacattt gatctgactg gaattcctcc tgctcctcgt ggggtcccac     180
agattgaagt cacctttgag atagatgtga atggtattct tcgagtgaca gctgaagaca    240
agggtacagg gaacaaaaat aagatcacaa tcaccaatga ccagaatcgc ctgacacctg    300
aagaaatcga aggatggtt aatgatgctg agaagtttgc tgaggaagac aaaaagctca     360
angagcgcat tgatactaag aaatgagttg gaaagctatg cctattctct aaagaatcag    420
attggngata aanaaaagct gggaggtaaa ctttcctctg aagataagga gaccatggaa    480
aaagctgtag aagaaaagat tgaatggctg gaaacccacc atgatgctga cattgaagac    540
ttcaaagcta agaagaagaa ctggaagaaa ttgttcaacc aattatcagc aaactctatg    600
ggaantgnag gcctccct                                                   618

<210> SEQ ID NO 5
<211> LENGTH: 619
<212> TYPE: DNA
<213> ORGANISM: Homo sapiens
<220> FEATURE:
<221> NAME/KEY: misc_feature
<222> LOCATION: (464)..(464)
<223> OTHER INFORMATION: The "n" at position 464 may be any of g, a,
      t, or c.
<220> FEATURE:
<221> NAME/KEY: misc_feature
<222> LOCATION: (486)..(486)
<223> OTHER INFORMATION: The "n" at position 486 may be any of g, a,
      t, or c.
<220> FEATURE:
<221> NAME/KEY: misc_feature
<222> LOCATION: (495)..(496)
<223> OTHER INFORMATION: The "n" at positions 495-96 may be any of g,
      a, t, or c.
<220> FEATURE:
<221> NAME/KEY: misc_feature
<222> LOCATION: (501)..(501)
<223> OTHER INFORMATION: The "n" at position 501 may be any of g, a,
      t, or c.
<220> FEATURE:
<221> NAME/KEY: misc_feature
<222> LOCATION: (525)..(525)
<223> OTHER INFORMATION: The "n" at position 525 may be any of g, a,
      t, or c.
<220> FEATURE:
<221> NAME/KEY: misc_feature
<222> LOCATION: (598)..(598)
<223> OTHER INFORMATION: The "n" at position 598 may be any of g, a,
      t, or c.
<220> FEATURE:
<221> NAME/KEY: misc_feature
<222> LOCATION: (601)..(601)
<223> OTHER INFORMATION: The "n" at position 601 may be any of g, a,
      t, or c.
<220> FEATURE:
```

-continued

```
<221> NAME/KEY: misc_feature
<222> LOCATION: (603)..(603)
<223> OTHER INFORMATION: The "n" at position 603 may be any of g, a,
      t, or c.
<220> FEATURE:
<221> NAME/KEY: misc_feature
<222> LOCATION: (616)..(616)
<223> OTHER INFORMATION: The "n" at position 616 may be any of g, a,
      t, or c.

<400> SEQUENCE: 5
ctgataatca accaactgtt acaatcaagg tctatgaagg tgaaagaccc ctgacaaaag      60
acaatcatct tctgggtaca tttgatctga ctggaattcc tcctgctcct cgtggggtcc    120
cacagattga agtcaccttt gagatagatg tgaatggtat tcttcgagtg acagctgaag    180
acaagggtac agggaacaaa aataagatca caatcaccaa tgaccagaat cgcctgacac    240
ctgaagaaat cgaaggatg gttaatgatg ctgagaagtt tgctgaggaa gacaaaagct     300
caaggagcgc attgatacta gaaatgagtt ggtaagctat gcctattctc taaagaatca    360
gattggtgat aaagaaaagc tgggaggtaa actttcctct gaagataatg agaccatgga    420
aaaagctgta gaagaaaaga ttgaatggct ggaaagccac caanatgctg acattgaaga    480
cttcanagct aagannaatg nactggaaga aattgttcaa ccaantatca gcaaactcta    540
tggaagtgca ggccctcccc caaccggtga atatggtaca gcagaaaaag atgagttnta    600
nanactgatc tgctanttg                                                  619

<210> SEQ ID NO 6
<211> LENGTH: 69
<212> TYPE: PRT
<213> ORGANISM: Homo sapiens

<400> SEQUENCE: 6

Trp Asn Asp Pro Arg Gly His Glu Gly Pro Ala Ser Asp Asn Gln Pro
 1               5                  10                  15

Thr Val Thr Ile Lys Val Tyr Glu Gly Glu Arg Pro Leu Thr Lys Asp
             20                  25                  30

Asn His Leu Leu Gly Thr Phe Val Pro Thr Gly Ile Pro Pro Ala Pro
         35                  40                  45

Arg Gly Val Pro Gln Ile Glu Val Thr Phe Glu Ile Asp Val Asn Gly
     50                  55                  60

Ile Leu Arg Ser Asp
 65

<210> SEQ ID NO 7
<211> LENGTH: 199
<212> TYPE: PRT
<213> ORGANISM: Homo sapiens

<400> SEQUENCE: 7

His Glu Gly Pro Ala Ser Asp Asn Gln Pro Thr Val Thr Ile Lys Val
 1               5                  10                  15

Tyr Glu Gly Glu Arg Pro Leu Thr Lys Asp Asn His Leu Leu Gly Thr
             20                  25                  30

Phe Asp Leu Thr Gly Ile Pro Pro Ala Pro Arg Gly Val Pro Gln Ile
         35                  40                  45

Glu Val Thr Phe Glu Ile Asp Val Asn Gly Ile Leu Arg Val Thr Ala
     50                  55                  60

Glu Asp Lys Gly Thr Gly Asn Lys Asn Lys Ile Thr Ile Thr Asn Asp
 65                  70                  75                  80
```

-continued

```
Gln Asn Arg Leu Thr Pro Glu Glu Ile Glu Arg Met Val Asn Asp Ala
                85                  90                  95
Glu Lys Phe Ala Glu Glu Asp Lys Lys Leu Lys Glu Arg Ile Asp Thr
            100                 105                 110
Arg Asn Glu Leu Glu Ser Tyr Ala Tyr Ser Leu Lys Asn Gln Ile Gly
        115                 120                 125
Asp Lys Glu Lys Leu Gly Gly Lys Leu Ser Ser Glu Asp Lys Glu Thr
    130                 135                 140
Met Glu Lys Ala Val Glu Glu Lys Ile Glu Trp Leu Glu Ser His Gln
145                 150                 155                 160
Asp Ala Asp Ile Val Asp Phe Lys Ala Asn Glu Gly Thr Gly Ile Asn
                165                 170                 175
Cys Ser Ser Asn Tyr Gln Gln Thr Pro Met Glu Val Gln Ala Leu Pro
            180                 185                 190
Gln Leu Val Lys Met Gln Ser
        195

<210> SEQ ID NO 8
<211> LENGTH: 253
<212> TYPE: PRT
<213> ORGANISM: Homo sapiens

<400> SEQUENCE: 8

Ala Gly Val Leu Ser Gly Asp Gln Asp Thr Gly Asp Leu Val Leu Leu
1               5                   10                  15
His Val Cys Pro Leu Thr Leu Gly Ile Glu Thr Val Gly Gly Val Met
                20                  25                  30
Thr Lys Leu Ile Pro Ser Asn Thr Val Val Pro Thr Lys Asn Ser Gln
            35                  40                  45
Ile Phe Ser Thr Ala Ser Asp Asn Gln Pro Thr Val Thr Ile Lys Val
        50                  55                  60
Tyr Glu Gly Glu Arg Pro Leu Thr Lys Asp Asn His Leu Leu Gly Thr
65                  70                  75                  80
Phe Asp Leu Thr Gly Ile Pro Pro Ala Pro Arg Gly Val Pro Gln Ile
                85                  90                  95
Glu Val Thr Phe Glu Ile Asp Val Asn Gly Ile Leu Arg Val Thr Ala
            100                 105                 110
Glu Asp Lys Gly Thr Gly Asn Lys Asn Lys Ile Thr Ile Thr Asn Asp
        115                 120                 125
Gln Asn Arg Leu Thr Pro Glu Glu Ile Glu Arg Met Val Asn Asp Ala
    130                 135                 140
Glu Lys Phe Ala Glu Glu Asp Lys Lys Leu Lys Glu Arg Ile Asp Thr
145                 150                 155                 160
Arg Asn Glu Leu Glu Ser Tyr Ala Tyr Ser Leu Lys Asn Gln Ile Gly
                165                 170                 175
Asp Lys Glu Lys Leu Gly Gly Lys Leu Ser Ser Glu Asp Lys Glu Thr
            180                 185                 190
Met Glu Lys Ala Val Glu Glu Lys Ile Glu Trp Leu Glu Ser His Gln
        195                 200                 205
Asp Ala Asp Ile Glu Asp Phe Lys Ala Lys Lys Lys Glu Leu Glu Glu
    210                 215                 220
Ile Val Gln Pro Ile Ile Ser Lys Leu Tyr Gly Ser Ala Gly Pro Pro
225                 230                 235                 240
Pro Thr Gly Glu Glu Asp Thr Ala Glu Lys Asp Glu Leu
```

-continued

<210> SEQ ID NO 9
<211> LENGTH: 196
<212> TYPE: PRT
<213> ORGANISM: Homo sapiens
<220> FEATURE:
<221> NAME/KEY: MISC_FEATURE
<222> LOCATION: (124)..(124)
<223> OTHER INFORMATION: The "Xaa" at position 124 may be any amino
    acid residue.
<220> FEATURE:
<221> NAME/KEY: MISC_FEATURE
<222> LOCATION: (143)..(144)
<223> OTHER INFORMATION: The "Xaa" at positions 143-144 may be any
    amino acid residue.
<220> FEATURE:
<221> NAME/KEY: MISC_FEATURE
<222> LOCATION: (192)..(193)
<223> OTHER INFORMATION: The "Xaa" at positions 192-193 may be any
    amino acid residue.

<400> SEQUENCE: 9

His Glu Gly Arg Pro Arg Arg Pro Thr Val Val Pro Thr Lys Lys Ser
1               5                   10                  15

Gln Ile Phe Ser Thr Ala Ser Asp Asn Gln Pro Thr Val Thr Ile Lys
            20                  25                  30

Val Tyr Glu Gly Glu Arg Pro Leu Thr Lys Asp Asn His Leu Leu Gly
        35                  40                  45

Thr Phe Asp Leu Thr Gly Ile Pro Pro Ala Pro Arg Gly Val Pro Gln
    50                  55                  60

Ile Glu Val Thr Phe Glu Ile Asp Val Asn Gly Ile Leu Arg Val Thr
65                  70                  75                  80

Ala Glu Asp Lys Gly Thr Gly Asn Lys Asn Lys Ile Thr Ile Thr Asn
                85                  90                  95

Asp Gln Asn Arg Leu Thr Pro Glu Glu Ile Glu Arg Met Val Asn Asp
            100                 105                 110

Ala Glu Lys Phe Ala Glu Glu Asp Lys Lys Leu Xaa Glu Arg Ile Asp
        115                 120                 125

Thr Lys Gly Lys Leu Cys Leu Phe Ser Lys Glu Ser Asp Trp Xaa Xaa
    130                 135                 140

Lys Ala Gly Arg Thr Phe Leu Arg Gly Asp His Gly Lys Ser Cys Arg
145                 150                 155                 160

Arg Lys Asp Met Ala Gly Lys Pro Pro Cys His Arg Leu Gln Glu Glu
                165                 170                 175

Glu Leu Glu Glu Ile Val Gln Pro Ile Ile Ser Lys Leu Tyr Gly Xaa
            180                 185                 190

Xaa Arg Pro Pro
        195

<210> SEQ ID NO 10
<211> LENGTH: 192
<212> TYPE: PRT
<213> ORGANISM: Homo sapiens
<220> FEATURE:
<221> NAME/KEY: MISC_FEATURE
<222> LOCATION: (146)..(146)
<223> OTHER INFORMATION: The "Xaa" at position 146 may be any amino
    acid residue.
<220> FEATURE:
<221> NAME/KEY: MISC_FEATURE
<222> LOCATION: (153)..(153)
<223> OTHER INFORMATION: The "Xaa" at position 153 may be any amino
    acid residue.

```
<220> FEATURE:
<221> NAME/KEY: MISC_FEATURE
<222> LOCATION: (156)..(156)
<223> OTHER INFORMATION: The "Xaa" at position 156 may be any amino
      acid residue.
<220> FEATURE:
<221> NAME/KEY: MISC_FEATURE
<222> LOCATION: (158)..(158)
<223> OTHER INFORMATION: The "Xaa" at position 158 may be any amino
      acid residue.
<220> FEATURE:
<221> NAME/KEY: MISC_FEATURE
<222> LOCATION: (164)..(164)
<223> OTHER INFORMATION: The "Xaa" at position 164 may be any amino
      acid residue.
<220> FEATURE:
<221> NAME/KEY: MISC_FEATURE
<222> LOCATION: (187)..(189)
<223> OTHER INFORMATION: The "Xaa" at positions 187-189 may be any
      amino acid residue.
<220> FEATURE:
<221> NAME/KEY: MISC_FEATURE
<222> LOCATION: (192)..(192)
<223> OTHER INFORMATION: The "Xaa" at position 192 may be any amino
      acid residue.

<400> SEQUENCE: 10

His Glu Pro Asp Asn Gln Pro Thr Val Thr Ile Lys Val Tyr Glu Gly
1               5                   10                  15

Glu Arg Pro Leu Thr Lys Asp Asn His Leu Leu Gly Thr Phe Asp Leu
            20                  25                  30

Thr Gly Ile Pro Pro Ala Pro Arg Gly Val Pro Gln Ile Glu Val Thr
        35                  40                  45

Phe Glu Ile Asp Val Asn Gly Ile Leu Arg Val Thr Ala Glu Asp Lys
    50                  55                  60

Gly Thr Gly Asn Lys Asn Lys Ile Thr Ile Thr Asn Asp Gln Asn Arg
65                  70                  75                  80

Leu Thr Pro Glu Glu Ile Glu Arg Met Val Asn Asp Ala Glu Lys Phe
                85                  90                  95

Ala Glu Glu Asp Lys Ser Ser Ser Ala Ile Leu Glu Met Ser Trp Met
            100                 105                 110

Pro Ile Leu Ile Arg Val Ile Lys Lys Ser Trp Glu Val Asn Phe Pro
        115                 120                 125

Leu Lys Ile Met Arg Pro Trp Lys Lys Leu Lys Lys Asn Gly Trp Lys
    130                 135                 140

Thr Xaa Met Leu Thr Lys Thr Ser Xaa Leu Arg Xaa Met Xaa Trp Lys
145                 150                 155                 160

Lys Phe Gln Xaa Ser Ala Asn Ser Met Glu Val Gln Ala Leu Pro Gln
                165                 170                 175

Pro Val Asn Met Gln Gln Lys Lys Met Ser Xaa Xaa Xaa Ser Ala Xaa
            180                 185                 190

<210> SEQ ID NO 11
<211> LENGTH: 222
<212> TYPE: PRT
<213> ORGANISM: Homo sapiens
<220> FEATURE:
<221> NAME/KEY: MISC_FEATURE
<222> LOCATION: (21)..(21)
<223> OTHER INFORMATION: The "Xaa" at position 21 may be any amino
      acid residue.
<220> FEATURE:
<221> NAME/KEY: MISC_FEATURE
<222> LOCATION: (36)..(36)
<223> OTHER INFORMATION: The "Xaa" at position 36 may be any amino
      acid residue.
```

```
<220> FEATURE:
<221> NAME/KEY: MISC_FEATURE
<222> LOCATION: (46)..(46)
<223> OTHER INFORMATION: The "Xaa" at position 46 may be any amino
      acid residue.
<220> FEATURE:
<221> NAME/KEY: MISC_FEATURE
<222> LOCATION: (59)..(61)
<223> OTHER INFORMATION: The "Xaa" at positions 59-61 may be any
      amino acid residue.
<220> FEATURE:
<221> NAME/KEY: MISC_FEATURE
<222> LOCATION: (67)..(67)
<223> OTHER INFORMATION: The "Xaa" at position 67 may be any amino
      acid residue.
<220> FEATURE:
<221> NAME/KEY: MISC_FEATURE
<222> LOCATION: (72)..(73)
<223> OTHER INFORMATION: The "Xaa" at positions 72-73 may be any
      amino acid residue.
<220> FEATURE:
<221> NAME/KEY: MISC_FEATURE
<222> LOCATION: (77)..(77)
<223> OTHER INFORMATION: The "Xaa" at position 77 may be any amino
      acid residue.
<220> FEATURE:
<221> NAME/KEY: MISC_FEATURE
<222> LOCATION: (79)..(80)
<223> OTHER INFORMATION: The "Xaa" at positions 79-80 may be any
      amino acid residue.
<220> FEATURE:
<221> NAME/KEY: MISC_FEATURE
<222> LOCATION: (82)..(82)
<223> OTHER INFORMATION: The "Xaa" at position 82 may be any
      amino acid residue.
<220> FEATURE:
<221> NAME/KEY: MISC_FEATURE
<222> LOCATION: (84)..(84)
<223> OTHER INFORMATION: The "Xaa" at position 84 may be any amino
      acid residue.
<220> FEATURE:
<221> NAME/KEY: MISC_FEATURE
<222> LOCATION: (91)..(91)
<223> OTHER INFORMATION: The "Xaa" at position 91 may be any amino
      acid residue.
<220> FEATURE:
<221> NAME/KEY: MISC_FEATURE
<222> LOCATION: (97)..(98)
<223> OTHER INFORMATION: The "Xaa" at positions 97-98 may be any
      amino acid residue.
<220> FEATURE:
<221> NAME/KEY: MISC_FEATURE
<222> LOCATION: (110)..(110)
<223> OTHER INFORMATION: The "Xaa" at position 110 may be any
      amino acid residue.
<220> FEATURE:
<221> NAME/KEY: MISC_FEATURE
<222> LOCATION: (123)..(124)
<223> OTHER INFORMATION: The "Xaa" at positions 123-124 may be
      any amino acid residue.
<220> FEATURE:
<221> NAME/KEY: MISC_FEATURE
<222> LOCATION: (128)..(129)
<223> OTHER INFORMATION: The "Xaa" at positions 128-129 may be any
      amino acid residue.
<220> FEATURE:
<221> NAME/KEY: MISC_FEATURE
<222> LOCATION: (133)..(133)
<223> OTHER INFORMATION: The "Xaa" at position 133 may be any
      amino acid residue.
<220> FEATURE:
<221> NAME/KEY: MISC_FEATURE
<222> LOCATION: (135)..(138)
<223> OTHER INFORMATION: The "Xaa" at positions 135-138 may be
      any amino acid residue.
<220> FEATURE:
<221> NAME/KEY: MISC_FEATURE
<222> LOCATION: (142)..(146)
<223> OTHER INFORMATION: The "Xaa" at positions 142-146 may be
```

```
      any amino acid residue.
<220> FEATURE:
<221> NAME/KEY: MISC_FEATURE
<222> LOCATION: (149)..(149)
<223> OTHER INFORMATION: The "Xaa" at position 149 may be any
      amino acid residue.
<220> FEATURE:
<221> NAME/KEY: MISC_FEATURE
<222> LOCATION: (151)..(151)
<223> OTHER INFORMATION: The "Xaa" at position 151 may be any
      amino acid residue.
<220> FEATURE:
<221> NAME/KEY: MISC_FEATURE
<222> LOCATION: (153)..(153)
<223> OTHER INFORMATION: The "Xaa" at position 153 may be any
      amino acid residue.
<220> FEATURE:
<221> NAME/KEY: MISC_FEATURE
<222> LOCATION: (156)..(156)
<223> OTHER INFORMATION: The "Xaa" at position 156 may be any
      amino acid residue.
<220> FEATURE:
<221> NAME/KEY: MISC_FEATURE
<222> LOCATION: (158)..(158)
<223> OTHER INFORMATION: The "Xaa" at position 158 may be any
      amino acid residue.
<220> FEATURE:
<221> NAME/KEY: MISC_FEATURE
<222> LOCATION: (162)..(163)
<223> OTHER INFORMATION: The "Xaa" at positions 162-163 may be
      any amino acid residue.
<220> FEATURE:
<221> NAME/KEY: MISC_FEATURE
<222> LOCATION: (165)..(165)
<223> OTHER INFORMATION: The "Xaa" at position 165 may be any
      amino acid residue.
<220> FEATURE:
<221> NAME/KEY: MISC_FEATURE
<222> LOCATION: (170)..(171)
<223> OTHER INFORMATION: The "Xaa" at positions 170-171 may be
      any amino acid residue.
<220> FEATURE:
<221> NAME/KEY: MISC_FEATURE
<222> LOCATION: (173)..(174)
<223> OTHER INFORMATION: The "Xaa" at positions 173-174 may be
      any amino acid residue.
<220> FEATURE:
<221> NAME/KEY: MISC_FEATURE
<222> LOCATION: (178)..(179)
<223> OTHER INFORMATION: The "Xaa" at positions 178-179 may be
      any amino acid residue.
<220> FEATURE:
<221> NAME/KEY: MISC_FEATURE
<222> LOCATION: (181)..(182)
<223> OTHER INFORMATION: The "Xaa" at positions 181-182 may be
      any amino acid residue.
<220> FEATURE:
<221> NAME/KEY: MISC_FEATURE
<222> LOCATION: (184)..(187)
<223> OTHER INFORMATION: The "Xaa" at positions 184-187 may be
      any amino acid residue.
<220> FEATURE:
<221> NAME/KEY: MISC_FEATURE
<222> LOCATION: (189)..(189)
<223> OTHER INFORMATION: The "Xaa" at position 189 may be any
      amino acid residue.
<220> FEATURE:
<221> NAME/KEY: MISC_FEATURE
<222> LOCATION: (192)..(192)
<223> OTHER INFORMATION: The "Xaa" at position 192 may be any
      amino acid residue.
<220> FEATURE:
<221> NAME/KEY: MISC_FEATURE
<222> LOCATION: (195)..(195)
<223> OTHER INFORMATION: The "Xaa" at position 195 may be any
      amino acid residue.
<220> FEATURE:
<221> NAME/KEY: MISC_FEATURE
<222> LOCATION: (197)..(197)
```

```
<223> OTHER INFORMATION: The "Xaa" at position 197 may be any
      amino acid residue.
<220> FEATURE:
<221> NAME/KEY: MISC_FEATURE
<222> LOCATION: (199)..(199)
<223> OTHER INFORMATION: The "Xaa" at position 199 may be any
      amino acid residue.
<220> FEATURE:
<221> NAME/KEY: MISC_FEATURE
<222> LOCATION: (203)..(204)
<223> OTHER INFORMATION: The "Xaa" at positions 203-204 may be
      any amino acid residue.
<220> FEATURE:
<221> NAME/KEY: MISC_FEATURE
<222> LOCATION: (208)..(208)
<223> OTHER INFORMATION: The "Xaa" at position 208 may be any
      amino acid residue.
<220> FEATURE:
<221> NAME/KEY: MISC_FEATURE
<222> LOCATION: (210)..(210)
<223> OTHER INFORMATION: The "Xaa" at position 210 may be any
      amino acid residue.
<220> FEATURE:
<221> NAME/KEY: MISC_FEATURE
<222> LOCATION: (212)..(213)
<223> OTHER INFORMATION: The "Xaa" at positions 212-213 may be
      any amino acid residue.
<220> FEATURE:
<221> NAME/KEY: MISC_FEATURE
<222> LOCATION: (215)..(215)
<223> OTHER INFORMATION: The "Xaa" at position 215 may be any
      amino acid residue.
<220> FEATURE:
<221> NAME/KEY: MISC_FEATURE
<222> LOCATION: (218)..(218)
<223> OTHER INFORMATION: The "Xaa" at position 218 may be any
      amino acid residue.
<220> FEATURE:
<221> NAME/KEY: MISC_FEATURE
<222> LOCATION: (220)..(220)
<223> OTHER INFORMATION: The "Xaa" at position 220 may be any
      amino acid residue.

<400> SEQUENCE: 11

His Glu Pro Asp Asn Gln Pro Thr Val Thr Ile Lys Val Tyr Glu Gly
1               5                   10                  15

Glu Arg Pro Leu Xaa Lys Asp Asn His Leu Leu Gly Thr Phe Asp Leu
            20                  25                  30

Thr Asn Ile Xaa Pro Ala Pro Arg Gly Val Pro Gln Ile Xaa His Leu
        35                  40                  45

Asp Arg Cys Glu Trp Tyr Ser Ser Ser Asp Xaa Xaa Xaa Asp Lys Gly
50                  55                  60

Thr Gly Xaa Lys Thr Lys Ile Xaa Xaa Thr Lys Ser Xaa Ile Xaa Xaa
65                  70                  75                  80

Leu Xaa Lys Xaa Lys Gly Trp Met Met Leu Xaa Lys Phe Ala Glu Glu
        85                  90                  95

Xaa Xaa Lys Leu Lys Glu Arg Ile Asp Ile Arg Ser Glu Xaa Glu Ser
            100                 105                 110

Tyr Ala Tyr Ser Leu Asn Gln Ile Gly Asp Xaa Xaa Ala Gly Arg Xaa
            115                 120                 125

Xaa Ser Ser Arg Xaa Gly Xaa Xaa Xaa Glu Ala Val Xaa Xaa Xaa
        130                 135                 140

Xaa Xaa Leu Glu Xaa Leu Xaa Lys Xaa Ala His Xaa Lys Xaa Asn Ser
145                 150                 155                 160

Leu Xaa Xaa Lys Xaa Thr Gly Tyr Lys Xaa Xaa Ser Xaa Xaa Leu Ser
            165                 170                 175

Ser Xaa Xaa His Xaa Xaa Val Xaa Xaa Xaa Xaa Ser Xaa Thr Gly Xaa
```

```
                    180                 185                 190
Arg Phe Xaa Gln Xaa Lys Xaa Leu Ser Leu Xaa Xaa Thr Gly Ser Xaa
            195                 200                 205
Val Xaa Val Xaa Xaa Val Xaa Tyr Gly Xaa Ser Xaa Glu Leu
    210                 215                 220

<210> SEQ ID NO 12
<211> LENGTH: 633
<212> TYPE: PRT
<213> ORGANISM: Homo sapiens

<400> SEQUENCE: 12

Arg Leu Arg Asn Gly His Val Gly Ile Ser Phe Val Pro Lys Glu Thr
1               5                   10                  15
Gly Glu His Leu Val His Val Lys Lys Asn Gly Gln His Val Ala Ser
            20                  25                  30
Ser Pro Ile Pro Val Val Ile Ser Gln Ser Glu Ile Gly Asp Ala Ser
        35                  40                  45
Arg Val Arg Val Ser Gly Gln Gly Leu His Lys Gly His Thr Phe Glu
    50                  55                  60
Pro Ala Glu Phe Ile Ile Asp Thr Arg Asp Ala Gly Tyr Gly Gly Leu
65                  70                  75                  80
Ser Leu Ser Ile Glu Gly Pro Ser Lys Val Asp Ile Asn Thr Glu Asp
                85                  90                  95
Leu Glu Asp Gly Thr Cys Arg Val Thr Tyr Cys Pro Thr Glu Pro Gly
            100                 105                 110
Asn Tyr Ile Ile Asn Ile Lys Phe Ala Asp Gln His Val Pro Gly Ser
        115                 120                 125
Pro Phe Ser Val Lys Val Thr Gly Glu Gly Arg Val Lys Glu Ser Ile
    130                 135                 140
Thr Arg Arg Arg Arg Ala Pro Ser Val Ala Asn Val Gly Ser His Cys
145                 150                 155                 160
Asp Leu Ser Leu Lys Ile Pro Glu Ile Ser Ile Gln Asp Met Thr Ala
                165                 170                 175
Gln Val Thr Ser Pro Ser Gly Lys Thr His Glu Ala Glu Ile Val Glu
            180                 185                 190
Gly Glu Asn His Thr Tyr Cys Ile Arg Phe Val Pro Ala Glu Met Gly
        195                 200                 205
Thr His Thr Val Ser Val Lys Tyr Lys Gly Gln His Val Pro Gly Ser
    210                 215                 220
Pro Phe Gln Phe Thr Val Gly Pro Leu Gly Glu Gly Gly Ala His Lys
225                 230                 235                 240
Val Arg Ala Gly Gly Pro Gly Leu Glu Glu Gly Val Pro Glu Phe Ser
                245                 250                 255
Trp Thr Arg Glu Ala Gly Ala Gly Leu Ala Ala Val Glu Pro Lys Ala
            260                 265                 270
Glu Ile Ser Phe Glu Asp Arg Asp Ser Cys Gly Ala Tyr Val Gln Glu
        275                 280                 285
Pro Gly Asp Tyr Glu Val Ser Val Lys Phe Asn Glu Glu His Ile Pro
    290                 295                 300
Asp Ser Pro Phe Val Val Pro Val Ala Ser Pro Ser Gly Asp Ala Arg
305                 310                 315                 320
Arg Leu Thr Val Ser Ser Leu Gln Glu Ser Gly Leu Lys Val Asn Gln
                325                 330                 335
```

-continued

```
Pro Ala Ser Phe Ala Val Ser Leu Asn Gly Ala Lys Gly Ala Ile Asp
            340                 345                 350

Ala Lys Val His Ser Pro Ser Gly Ala Leu Glu Glu Cys Tyr Val Thr
            355                 360                 365

Glu Ile Asp Gln Asp Lys Tyr Ala Val Arg Phe Ile Pro Arg Glu Asn
            370                 375                 380

Gly Val Tyr Leu Ile Asp Val Lys Phe Asn Gly Thr His Ile Pro Gly
385                 390                 395                 400

Ser Pro Phe Lys Ile Arg Val Gly Glu Pro Gly His Gly Gly Asp Pro
                405                 410                 415

Gly Leu Val Ser Ala Tyr Gly Ala Gly Leu Glu Gly Gly Val Thr Gly
                420                 425                 430

Asn Pro Ala Glu Phe Val Val Asn Thr Ser Asn Ala Gly Ala Gly Ala
            435                 440                 445

Leu Ser Val Thr Ile Asp Gly Pro Ser Lys Val Lys Met Asp Cys Gln
            450                 455                 460

Glu Cys Pro Glu Gly Tyr Arg Val Thr Tyr Thr Pro Met Ala Pro Gly
465                 470                 475                 480

Ser Tyr Leu Ile Ser Ile Lys Tyr Gly Gly Pro Tyr His Ile Gly Gly
                485                 490                 495

Ser Pro Phe Lys Ala Lys Val Thr Gly Pro Arg Leu Val Ser Asn His
            500                 505                 510

Ser Leu His Glu Thr Ser Ser Val Phe Val Asp Ser Leu Thr Lys Ala
            515                 520                 525

Thr Cys Ala Pro Gln His Gly Ala Pro Gly Pro Gly Pro Ala Asp Ala
            530                 535                 540

Ser Lys Val Val Ala Lys Gly Leu Gly Leu Ser Lys Ala Tyr Val Gly
545                 550                 555                 560

Gln Lys Ser Ser Phe Thr Val Asp Cys Ser Lys Ala Gln Asn Asn Met
                565                 570                 575

Leu Leu Val Gly Val His Gly Pro Arg Thr Pro Cys Glu Glu Ile Leu
            580                 585                 590

Val Lys His Val Gly Ser Arg Leu Tyr Ser Val Ser Tyr Leu Leu Lys
            595                 600                 605

Asp Lys Gly Glu Tyr Thr Leu Val Val Lys Trp Gly His Glu His Ile
            610                 615                 620

Pro Gly Ser Pro Tyr Arg Val Val Pro
625                 630
```

<210> SEQ ID NO 13
<211> LENGTH: 212
<212> TYPE: PRT
<213> ORGANISM: Homo sapiens

<400> SEQUENCE: 13

```
His Glu Gly Arg Gly Val Thr Gly Asn Pro Ala Glu Phe Val Val Asn
1               5                   10                  15

Thr Ser Asn Ala Gly Ala Gly Ala Leu Ser Val Thr Ile Asp Gly Pro
            20                  25                  30

Ser Lys Val Lys Met Asp Cys Gln Glu Cys Pro Glu Gly Tyr Arg Val
            35                  40                  45

Thr Tyr Thr Pro Met Ala Pro Gly Ser Tyr Leu Ile Ser Ile Lys Tyr
            50                  55                  60

Gly Gly Pro Tyr His Ile Gly Gly Ser Pro Phe Lys Ala Lys Val Thr
65                  70                  75                  80
```

```
Gly Pro Arg Leu Val Ser Asn His Ser Leu His Glu Thr Ser Ser Val
                85                  90                  95

Phe Val Asp Ser Leu Thr Lys Ala Thr Cys Ala Pro His His Gly Ala
            100                 105                 110

Pro Gly Pro Gly Pro Ala Asp Ala Ser Lys Val Val Ala Lys Gly Leu
        115                 120                 125

Gly Leu Ser Lys Ala Tyr Val Cys His Lys Ser Ser Phe Thr Val Asp
    130                 135                 140

Cys Ser Lys Ala Cys Ile Ile Met Leu Leu Val Gly Val His Gly Pro
145                 150                 155                 160

Trp Thr Pro Cys Asp Glu Ile Leu Val Lys Ala Arg Gly Gln Pro Ala
                165                 170                 175

Leu Gln Arg Val Leu Thr Cys Phe Lys Asp Lys Gly Glu Val His Thr
                180                 185                 190

Gly Gly Gln Asn Gly Gly Asp Tyr Gln Ile Pro Cys Lys Pro Leu Pro
            195                 200                 205

Cys Gly Cys Pro
        210

<210> SEQ ID NO 14
<211> LENGTH: 200
<212> TYPE: PRT
<213> ORGANISM: Homo sapiens
<220> FEATURE:
<221> NAME/KEY: MISC_FEATURE
<222> LOCATION: (137)..(137)
<223> OTHER INFORMATION: The "Xaa" at position 137 may be any
      amino acid residue.
<220> FEATURE:
<221> NAME/KEY: MISC_FEATURE
<222> LOCATION: (146)..(146)
<223> OTHER INFORMATION: The "Xaa" at position 146 may be any
      amino acid residue.
<220> FEATURE:
<221> NAME/KEY: MISC_FEATURE
<222> LOCATION: (166)..(166)
<223> OTHER INFORMATION: The "Xaa" at position 166 may be any
      amino acid residue.
<220> FEATURE:
<221> NAME/KEY: MISC_FEATURE
<222> LOCATION: (168)..(168)
<223> OTHER INFORMATION: The "Xaa" at position 168 may be any
      amino acid residue.
<220> FEATURE:
<221> NAME/KEY: MISC_FEATURE
<222> LOCATION: (170)..(170)
<223> OTHER INFORMATION: The "Xaa" at position 170 may be any
      amino acid residue.
<220> FEATURE:
<221> NAME/KEY: MISC_FEATURE
<222> LOCATION: (184)..(184)
<223> OTHER INFORMATION: The "Xaa" at position 184 may be any
      amino acid residue.
<220> FEATURE:
<221> NAME/KEY: MISC_FEATURE
<222> LOCATION: (189)..(189)
<223> OTHER INFORMATION: The "Xaa" at position 189 may be any
      amino acid residue.
<220> FEATURE:
<221> NAME/KEY: MISC_FEATURE
<222> LOCATION: (192)..(192)
<223> OTHER INFORMATION: The "Xaa" at position 192 may be any
      amino acid residue.
<220> FEATURE:
<221> NAME/KEY: MISC_FEATURE
<222> LOCATION: (200)..(200)
<223> OTHER INFORMATION: The "Xaa" at position 200 may be any
      amino acid residue.
```

```
<400> SEQUENCE: 14

His Glu Gly Arg Pro Thr Glu Pro Gly Asn Tyr Ile Ile Asn Ile Lys
1               5                   10                  15

Phe Ala Asp Gln His Val Pro Gly Ser Pro Phe Ser Val Lys Val Thr
                20                  25                  30

Gly Glu Gly Arg Val Lys Glu Ser Ile Thr Arg Arg Arg Arg Ala Pro
            35                  40                  45

Ser Val Ala Asn Val Gly Ser His Cys Asp Leu Ser Leu Lys Ile Pro
        50                  55                  60

Glu Ile Ser Ile Gln Asp Met Thr Ala Gln Val Thr Ser Pro Ser Gly
65                  70                  75                  80

Lys Thr His Glu Ala Glu Ile Val Glu Gly Glu Asn Thr His Thr Tyr Cys
                85                  90                  95

Ile Arg Phe Val Pro Ala Glu Met Gly Thr His Thr Val Ser Val Lys
            100                 105                 110

Tyr Lys Gly Gln His Val Pro Gly Ser Pro Phe Gln Phe Thr Val Gly
        115                 120                 125

Pro Leu Gly Glu Gly Gly Ala His Xaa Val Arg Ala Gly Gly Pro Gly
    130                 135                 140

Leu Xaa Trp Ser Ala Arg Ile Gln Tyr Gly Pro Gly Lys Leu Val Leu
145                 150                 155                 160

Glu Trp Pro Leu Ser Xaa Pro Xaa Leu Xaa Ser Leu Leu Arg Thr Ala
                165                 170                 175

Thr Pro Val Val Leu Met Val Xaa Glu Pro Ser Asp Xaa Asn Pro Xaa
            180                 185                 190

Gln Val Ser Thr Lys Glu His Xaa
        195                 200

<210> SEQ ID NO 15
<211> LENGTH: 195
<212> TYPE: PRT
<213> ORGANISM: Homo sapiens

<400> SEQUENCE: 15

His Glu Gly Arg Gly Val Pro Glu Asp Leu Leu Asn Gly Leu Lys Val
1               5                   10                  15

Thr Asp Thr Gln Glu Ala Glu Cys Ala Gly Pro Val Pro Asp Pro
                20                  25                  30

Lys Asn Gln His Ser Gln Ser Lys Leu Leu Arg Asp Asp Glu Ala His
            35                  40                  45

Leu Gln Glu Asp Gln Gly Glu Glu Cys Phe His Asp Cys Ser Ala
        50                  55                  60

Ser Phe Glu Glu Glu Pro Gly Ala Asp Lys Val Glu Asn Lys Ser Asn
65                  70                  75                  80

Glu Asp Val Asn Ser Ser Glu Leu Asp Glu Glu Tyr Leu Ile Glu Leu
                85                  90                  95

Glu Lys Asn Met Ser Asp Glu Glu Lys Gln Lys Arg Arg Glu Glu Ser
            100                 105                 110

Thr Arg Leu Lys Glu Glu Gly Asn Glu Gln Phe Lys Lys Gly Asp Tyr
        115                 120                 125

Ile Glu Ala Glu Ser Ser Tyr Ser Arg Ala Leu Glu Met Cys Pro Ser
    130                 135                 140

Cys Phe Gln Lys Glu Arg Ser Ile Leu Phe Ser Asn Arg Ala Ala Ala
145                 150                 155                 160
```

```
Arg Met Lys Gln Asp Lys Lys Glu Met Ala Ile Asn Asp Cys Ser Ile
            165                 170                 175

Ala Ile Gln Leu Asn Pro Ser Tyr Ile Arg Ala Ile Leu Arg Arg Ala
        180                 185                 190

Glu Phe Val
        195

<210> SEQ ID NO 16
<211> LENGTH: 292
<212> TYPE: PRT
<213> ORGANISM: Homo sapiens

<400> SEQUENCE: 16

Met Gly Glu Lys Ser Glu Asn Cys Gly Val Pro Glu Asp Leu Leu Asn
1               5                  10                  15

Gly Leu Lys Val Thr Asp Thr Gln Glu Ala Glu Cys Ala Gly Pro Pro
            20                  25                  30

Val Pro Asp Pro Lys Asn Gln His Ser Gln Ser Lys Leu Leu Arg Asp
        35                  40                  45

Asp Glu Ala His Leu Gln Glu Asp Gln Gly Glu Glu Cys Phe His
    50                  55                  60

Asp Cys Ser Ala Ser Phe Glu Glu Pro Gly Ala Asp Lys Val Glu
65                  70                  75                  80

Asn Lys Ser Asn Glu Asp Val Asn Ser Ser Glu Leu Asp Glu Glu Tyr
                85                  90                  95

Leu Ile Glu Leu Glu Lys Asn Met Ser Asp Glu Glu Lys Gln Lys Arg
            100                 105                 110

Arg Glu Glu Ser Thr Arg Leu Lys Glu Glu Gly Asn Glu Gln Phe Lys
            115                 120                 125

Lys Gly Asp Tyr Ile Glu Ala Glu Ser Ser Tyr Ser Arg Ala Leu Glu
130                 135                 140

Met Cys Pro Ser Cys Phe Gln Lys Glu Arg Ser Ile Leu Phe Ser Asn
145                 150                 155                 160

Arg Ala Ala Ala Arg Met Lys Gln Asp Lys Lys Glu Met Ala Ile Asn
                165                 170                 175

Asp Cys Ser Lys Ala Ile Gln Leu Asn Pro Ser Tyr Ile Arg Ala Ile
            180                 185                 190

Leu Arg Arg Ala Glu Leu Tyr Glu Lys Thr Asp Lys Leu Asp Glu Ala
        195                 200                 205

Leu Glu Asp Tyr Lys Ser Ile Leu Glu Lys Asp Pro Ser Ile His Gln
    210                 215                 220

Ala Arg Glu Ala Cys Met Arg Leu Pro Lys Gln Ile Glu Glu Arg Asn
225                 230                 235                 240

Glu Arg Leu Lys Glu Glu Met Leu Gly Lys Leu Lys Asp Leu Gly Asn
                245                 250                 255

Leu Val Leu Arg Pro Phe Gly Leu Ser Thr Glu Asn Phe Gln Ile Lys
            260                 265                 270

Gln Asp Ser Ser Thr Gly Ser Tyr Ser Ile Asn Phe Val Gln Asn Pro
        275                 280                 285

Asn Asn Asn Arg
    290

<210> SEQ ID NO 17
<211> LENGTH: 218
<212> TYPE: PRT
<213> ORGANISM: Homo sapiens
```

```
<220> FEATURE:
<221> NAME/KEY: MISC_FEATURE
<222> LOCATION: (35)..(35)
<223> OTHER INFORMATION: The "Xaa" at position 35 may be any
      amino acid residue.
<220> FEATURE:
<221> NAME/KEY: MISC_FEATURE
<222> LOCATION: (168)..(168)
<223> OTHER INFORMATION: The "Xaa" at position 168 may be any
      amino acid residue.
<220> FEATURE:
<221> NAME/KEY: MISC_FEATURE
<222> LOCATION: (178)..(178)
<223> OTHER INFORMATION: The "Xaa" at position 178 may be any
      amino acid residue.
<220> FEATURE:
<221> NAME/KEY: MISC_FEATURE
<222> LOCATION: (187)..(187)
<223> OTHER INFORMATION: The "Xaa" at position 187 may be any
      amino acid residue.
<220> FEATURE:
<221> NAME/KEY: MISC_FEATURE
<222> LOCATION: (200)..(200)
<223> OTHER INFORMATION: The "Xaa" at position 200 may be any
      amino acid residue.
<220> FEATURE:
<221> NAME/KEY: MISC_FEATURE
<222> LOCATION: (204)..(204)
<223> OTHER INFORMATION: The "Xaa" at position 204 may be any
      amino acid residue.
<220> FEATURE:
<221> NAME/KEY: MISC_FEATURE
<222> LOCATION: (206)..(206)
<223> OTHER INFORMATION: The "Xaa" at position 206 may be any
      amino acid residue.
<220> FEATURE:
<221> NAME/KEY: MISC_FEATURE
<222> LOCATION: (210)..(210)
<223> OTHER INFORMATION: The "Xaa" at position 210 may be any
      amino acid residue.
<220> FEATURE:
<221> NAME/KEY: MISC_FEATURE
<222> LOCATION: (214)..(215)
<223> OTHER INFORMATION: The "Xaa" at positions 214-215 may be
      any amino acid residue.

<400> SEQUENCE: 17

His Glu Gly Pro Ser Pro Ser Leu Gly Ser Met Gly Glu Lys Ser
 1               5                  10                  15

Glu Asn Cys Gly Val Pro Glu Asp Leu Leu Asn Gly Leu Lys Val Thr
                20                  25                  30

Asp Thr Xaa Glu Ala Glu Cys Ala Gly Pro Pro Val Pro Asp Pro Lys
            35                  40                  45

Asn Gln His Ser Gln Ser Lys Leu Leu Arg Asp Asp Glu Ala His Leu
     50                  55                  60

Gln Glu Asp Gln Gly Glu Glu Cys Phe His Asp Cys Ser Ala Ser
65                  70                  75                  80

Phe Glu Glu Glu Pro Gly Ala Asp Lys Val Glu Asn Lys Ser Asn Glu
                85                  90                  95

Asp Val Asn Ser Ser Glu Leu Asp Glu Glu Tyr Leu Ile Glu Leu Glu
                100                 105                 110

Lys Asn Met Ser Asp Glu Glu Lys Gln Lys Arg Arg Glu Glu Ser Thr
        115                 120                 125

Arg Leu Lys Glu Glu Gly Asn Glu Gln Phe Lys Lys Gly Asp Tyr Ile
    130                 135                 140

Glu Ala Glu Ser Ser Tyr Ser Arg Ala Leu Glu Met Cys Pro Ser Cys
145                 150                 155                 160

Phe Gln Lys Glu Arg Ser Ile Xaa Phe Ser Asn Arg Ala Ala Ala Arg
```

```
                      165                 170                 175
Met Xaa Gln Asp Lys Lys Glu Met Ala Ile Xaa Asp Cys Ser Lys Ala
            180                 185                 190

Phe Asn Thr Pro Thr Ile Ser Xaa Gln Tyr Gly Xaa Gln Xaa Cys Leu
        195                 200                 205

Arg Xaa Arg Thr Ser Xaa Xaa Pro Trp Met
    210                 215
```

<210> SEQ ID NO 18
<211> LENGTH: 209
<212> TYPE: PRT
<213> ORGANISM: Homo sapiens
<220> FEATURE:
<221> NAME/KEY: MISC_FEATURE
<222> LOCATION: (37)..(37)
<223> OTHER INFORMATION: The "Xaa" at position 37 may be any
      amino acid residue.
<220> FEATURE:
<221> NAME/KEY: MISC_FEATURE
<222> LOCATION: (131)..(131)
<223> OTHER INFORMATION: The "Xaa" at position 131 may be any
      amino acid residue.
<220> FEATURE:
<221> NAME/KEY: MISC_FEATURE
<222> LOCATION: (147)..(147)
<223> OTHER INFORMATION: The "Xaa" at position 147 may be any
      amino acid residue.
<220> FEATURE:
<221> NAME/KEY: MISC_FEATURE
<222> LOCATION: (167)..(167)
<223> OTHER INFORMATION: The "Xaa" at position 167 may be any
      amino acid residue.
<220> FEATURE:
<221> NAME/KEY: MISC_FEATURE
<222> LOCATION: (178)..(178)
<223> OTHER INFORMATION: The "Xaa" at position 178 may be any
      amino acid residue.
<220> FEATURE:
<221> NAME/KEY: MISC_FEATURE
<222> LOCATION: (180)..(180)
<223> OTHER INFORMATION: The "Xaa" at position 180 may be any
      amino acid residue.
<220> FEATURE:
<221> NAME/KEY: MISC_FEATURE
<222> LOCATION: (185)..(185)
<223> OTHER INFORMATION: The "Xaa" at position 185 may be any
      amino acid residue.
<220> FEATURE:
<221> NAME/KEY: MISC_FEATURE
<222> LOCATION: (193)..(193)
<223> OTHER INFORMATION: The "Xaa" at position 193 may be any
      amino acid residue.
<220> FEATURE:
<221> NAME/KEY: MISC_FEATURE
<222> LOCATION: (202)..(202)
<223> OTHER INFORMATION: The "Xaa" at position 202 may be any
      amino acid residue.
<220> FEATURE:
<221> NAME/KEY: MISC_FEATURE
<222> LOCATION: (204)..(204)
<223> OTHER INFORMATION: The "Xaa" at position 204 may be any
      amino acid residue.
<220> FEATURE:
<221> NAME/KEY: MISC_FEATURE
<222> LOCATION: (206)..(206)
<223> OTHER INFORMATION: The "Xaa" at position 206 may be any
      amino acid residue.
<220> FEATURE:
<221> NAME/KEY: MISC_FEATURE
<222> LOCATION: (208)..(208)
<223> OTHER INFORMATION: The "Xaa" at position 208 may be any
      amino acid residue.

<400> SEQUENCE: 18

-continued

```
His Gly Glu Pro Leu Ala Ser Pro Pro Ser Leu Gly Ser Met Gly Glu
1               5                   10                  15

Lys Ser Glu Asn Cys Gly Val Pro Gly Asp Leu Leu Asn Gly Leu Lys
                20                  25                  30

Val Thr Asp Thr Xaa Glu Ala Glu Cys Ala Gly Pro Pro Val Pro Asp
                35                  40                  45

Pro Lys Asn Gln His Ser Gln Ser Lys Leu Leu Arg Asp Asp Glu Ala
        50                  55                  60

His Leu Gln Glu Asp Gln Gly Glu Glu Glu Cys Phe His Asp Cys Ser
65                  70                  75                  80

Ala Ser Phe Glu Glu Glu Pro Gly Ala Asp Lys Val Glu Asn Lys Ser
                85                  90                  95

Asn Glu Asp Val Asn Ser Ser Glu Leu Asp Glu Glu Tyr Leu Ile Glu
                100                 105                 110

Leu Glu Lys Asn Met Ser Asp Glu Glu Lys Gln Lys Arg Arg Glu Glu
                115                 120                 125

Ser Thr Xaa Leu Lys Glu Glu Gly Asn Glu Gln Phe Lys Lys Gly Asp
        130                 135                 140

Tyr Ile Xaa Ala Glu Ser Ser Tyr Ser Arg Ala Leu Glu Met Cys Pro
145                 150                 155                 160

Ser Cys Phe Gln Lys Glu Xaa Ser Ile Leu Phe Ser Asn Thr Ala Ala
                165                 170                 175

Ala Xaa Asp Xaa Thr Gly Gln Glu Xaa Asn Gly His Pro Met Thr Ala
        180                 185                 190

Xaa Leu Gln Phe Asn Pro His Leu Tyr Xaa Gly Xaa Ile Xaa Asp Xaa
        195                 200                 205

Met
```

<210> SEQ ID NO 19
<211> LENGTH: 212
<212> TYPE: PRT
<213> ORGANISM: Homo sapiens
<220> FEATURE:
<221> NAME/KEY: MISC_FEATURE
<222> LOCATION: (7)..(7)
<223> OTHER INFORMATION: The "Xaa" at position 7 may be any
      amino acid residue.
<220> FEATURE:
<221> NAME/KEY: MISC_FEATURE
<222> LOCATION: (47)..(47)
<223> OTHER INFORMATION: The "Xaa" at position 47 may be any
      amino acid residue.
<220> FEATURE:
<221> NAME/KEY: MISC_FEATURE
<222> LOCATION: (92)..(92)
<223> OTHER INFORMATION: The "Xaa" at position 92 may be any
      amino acid residue.
<220> FEATURE:
<221> NAME/KEY: MISC_FEATURE
<222> LOCATION: (107)..(107)
<223> OTHER INFORMATION: The "Xaa" at position 107 may be any
      amino acid residue.
<220> FEATURE:
<221> NAME/KEY: MISC_FEATURE
<222> LOCATION: (113)..(113)
<223> OTHER INFORMATION: The "Xaa" at position 113 may be any
      amino acid residue.
<220> FEATURE:
<221> NAME/KEY: MISC_FEATURE
<222> LOCATION: (124)..(124)
<223> OTHER INFORMATION: The "Xaa" at position 124 may be any
      amino acid residue.
<220> FEATURE:
<221> NAME/KEY: MISC_FEATURE
<222> LOCATION: (128)..(129)

```
<223> OTHER INFORMATION: The "Xaa" at positions 128-29 may be
      any amino acid residue.
<220> FEATURE:
<221> NAME/KEY: MISC_FEATURE
<222> LOCATION: (135)..(135)
<223> OTHER INFORMATION: The "Xaa" at position 135 may be any
      amino acid residue.
<220> FEATURE:
<221> NAME/KEY: MISC_FEATURE
<222> LOCATION: (167)..(167)
<223> OTHER INFORMATION: The "Xaa" at position 167 may be any
      amino acid residue.
<220> FEATURE:
<221> NAME/KEY: MISC_FEATURE
<222> LOCATION: (174)..(174)
<223> OTHER INFORMATION: The "Xaa" at position 174 may be any
      amino acid residue.
<220> FEATURE:
<221> NAME/KEY: MISC_FEATURE
<222> LOCATION: (183)..(184)
<223> OTHER INFORMATION: The "Xaa" at positions 183-84 may be
      any amino acid residue.
<220> FEATURE:
<221> NAME/KEY: MISC_FEATURE
<222> LOCATION: (188)..(188)
<223> OTHER INFORMATION: The "Xaa" at position 188 may be any
      amino acid residue.
<220> FEATURE:
<221> NAME/KEY: MISC_FEATURE
<222> LOCATION: (190)..(190)
<223> OTHER INFORMATION: The "Xaa" at position 190 may be any
      amino acid residue.
<220> FEATURE:
<221> NAME/KEY: MISC_FEATURE
<222> LOCATION: (197)..(197)
<223> OTHER INFORMATION: The "Xaa" at position 197 may be any
      amino acid residue.
<220> FEATURE:
<221> NAME/KEY: MISC_FEATURE
<222> LOCATION: (202)..(203)
<223> OTHER INFORMATION: The "Xaa" at positions 202-203 may be
      any amino acid residue.
<220> FEATURE:
<221> NAME/KEY: MISC_FEATURE
<222> LOCATION: (206)..(206)
<223> OTHER INFORMATION: The "Xaa" at position 206 may be any
      amino acid residue.
<220> FEATURE:
<221> NAME/KEY: MISC_FEATURE
<222> LOCATION: (211)..(212)
<223> OTHER INFORMATION: The "Xaa" at positions 211-212 may be
      any amino acid residue.

<400> SEQUENCE: 19

His Glu Gly Arg Ser Leu Xaa Ser Pro Pro Ser Leu Gly Ser Met Gly
1               5                   10                  15

Glu Lys Ser Glu Asn Cys Gly Val Pro Glu Asp Leu Leu Asn Gly Leu
            20                  25                  30

Lys Val Thr Asp Thr Gln Glu Ala Glu Cys Ala Gly Pro Pro Xaa Pro
        35                  40                  45

Asp Pro Lys Asn Gln His Ser Gln Ser Lys Leu Leu Arg Asp Asp Glu
    50                  55                  60

Ala His Leu Gln Glu Asp Gln Gly Glu Glu Cys Phe His Asp Cys
65                  70                  75                  80

Ser Ala Ser Phe Glu Glu Glu Pro Gly Ala Asp Xaa Val Glu Asn Lys
                85                  90                  95

Ser Asn Glu Asp Val Asn Ser Ser Glu Leu Xaa Glu Glu Tyr Leu Ile
            100                 105                 110

Xaa Leu Glu Lys Asn Met Ser Asp Glu Glu Lys Xaa Lys Arg Arg Xaa
        115                 120                 125
```

```
Xaa Ser Thr Arg Leu Lys Xaa Glu Gly Asn Glu Gln Phe Lys Lys Gly
    130                 135                 140

Asp Tyr Ile Glu Ala Glu Ser Ser Tyr Lys Ser Ser Pro Arg Asn Val
145                 150                 155                 160

Pro Ile Leu Leu Pro Lys Xaa Glu Val Asp Ser Ile Phe Xaa Tyr Ser
                165                 170                 175

Cys Ser Lys Gly Asn Met Xaa Xaa Lys Lys Trp Xaa Ser Xaa Asp Cys
            180                 185                 190

Ser Lys Ala Phe Xaa Thr Pro Thr Tyr Xaa Xaa Asn Ile Xaa Asp Ile
            195                 200                 205

Arg Val Xaa Xaa
    210

<210> SEQ ID NO 20
<211> LENGTH: 745
<212> TYPE: DNA
<213> ORGANISM: Homo sapiens
<220> FEATURE:
<221> NAME/KEY: misc_feature
<222> LOCATION: (493)..(493)
<223> OTHER INFORMATION: The "n" at position 493 may be any of
      g, a, t, or c.
<220> FEATURE:
<221> NAME/KEY: misc_feature
<222> LOCATION: (510)..(510)
<223> OTHER INFORMATION: The "n" at position 510 may be any of
      g, a, t, or c.
<220> FEATURE:
<221> NAME/KEY: misc_feature
<222> LOCATION: (576)..(576)
<223> OTHER INFORMATION: The "n" at position 576 may be any of
      g, a, t, or c.
<220> FEATURE:
<221> NAME/KEY: misc_feature
<222> LOCATION: (590)..(590)
<223> OTHER INFORMATION: The "n" at position 590 may be any of
      g, a, t, or c.
<220> FEATURE:
<221> NAME/KEY: misc_feature
<222> LOCATION: (614)..(614)
<223> OTHER INFORMATION: The "n" at position 614 may be any of
      g, a, t, or c.
<220> FEATURE:
<221> NAME/KEY: misc_feature
<222> LOCATION: (630)..(630)
<223> OTHER INFORMATION: The "n" at position 630 may be any of
      g, a, t, or c.
<220> FEATURE:
<221> NAME/KEY: misc_feature
<222> LOCATION: (636)..(636)
<223> OTHER INFORMATION: The "n" at position 636 may be any of
      g, a, t, or c.
<220> FEATURE:
<221> NAME/KEY: misc_feature
<222> LOCATION: (657)..(658)
<223> OTHER INFORMATION: The "n" at positions 657-658 may be any
      of g, a, t, or c.
<220> FEATURE:
<221> NAME/KEY: misc_feature
<222> LOCATION: (660)..(660)
<223> OTHER INFORMATION: The "n" at position 660 may be any of
      g, a, t, or c.
<220> FEATURE:
<221> NAME/KEY: misc_feature
<222> LOCATION: (674)..(674)
<223> OTHER INFORMATION: The "n" at position 674 may be any of
      g, a, t, or c.
<220> FEATURE:
<221> NAME/KEY: misc_feature
<222> LOCATION: (685)..(685)
<223> OTHER INFORMATION: The "n" at position 685 may be any of
      g, a, t, or c.
<220> FEATURE:
```

```
<221> NAME/KEY: misc_feature
<222> LOCATION: (697)..(697)
<223> OTHER INFORMATION: The "n" at position 697 may be any of
      g, a, t, or c.
<220> FEATURE:
<221> NAME/KEY: misc_feature
<222> LOCATION: (699)..(699)
<223> OTHER INFORMATION: The "n" at position 699 may be any of
      g, a, t, or c.
<220> FEATURE:
<221> NAME/KEY: misc_feature
<222> LOCATION: (714)..(714)
<223> OTHER INFORMATION: The "n" at position 714 may be any of
      g, a, t, or c.
<220> FEATURE:
<221> NAME/KEY: misc_feature
<222> LOCATION: (719)..(719)
<223> OTHER INFORMATION: The "n" at position 719 may be any of
      g, a, t, or c.
<220> FEATURE:
<221> NAME/KEY: misc_feature
<222> LOCATION: (724)..(724)
<223> OTHER INFORMATION: The "n" at position 724 may be any of
      g, a, t, or c.
<220> FEATURE:
<221> NAME/KEY: misc_feature
<222> LOCATION: (730)..(730)
<223> OTHER INFORMATION: The "n" at position 730 may be any of
      g, a, t, or c.
<220> FEATURE:
<221> NAME/KEY: misc_feature
<222> LOCATION: (732)..(732)
<223> OTHER INFORMATION: The "n" at position 732 may be any of
      g, a, t, or c.

<400> SEQUENCE: 20
gtgatattat tgtagatcta gaagtcactt tggaagaagt atatgcagga aattttgtgg      60
aagtagttag aaacaaacct gtggcaaggc aggctcctgg caaacggaag tgcaattgtc     120
ggcaagagat gcggaccacc cagctgggcc ctgggcgctt ccaaatgacc caggaggtgg     180
tctgcgacga atgccctaat gtcaaactag tgaatgaaga acgaacgctg aagtagaaa      240 tagagcctgg ggtgagagac ggcatggagt acccctttat tggagaaggt gagcctcacg     300
tggatgggga gcctggagat ttacggttcc gaatcaaagt tgtcaagcac ccaatatttg     360
aaaggagagg agatgatttg tacacaaatg tgacaatctc attagttgag tcactggttg     420
gctttgagat ggatattact cacttggatg gtcacaaggt acatatttcc cgggataaag     480
atcaccaggc cangagcgaa tctatggaan aaggggaag ggctcccaa ctttgacaac       540 aacaatatca agggctcctt gataatcact tttgangtgg attttttccan aagaacagtt    600 acagaggaag ccanagaagt atcaaaaacan ctactnaaac aaagtcaatt cagaagnntn    660
caatggaccg caangatttg aaaantgaat aaattgncnt tgttaaaata attnattanc     720
catnattatn antcaaggtt ttttt                                           745

<210> SEQ ID NO 21
<211> LENGTH: 17
<212> TYPE: DNA
<213> ORGANISM: Artificial Sequence
<220> FEATURE:
<223> OTHER INFORMATION: Description of Artificial Sequence:
      pACT-specific sequencing primer

<400> SEQUENCE: 21
taccactaca atggatg                                                    17

<210> SEQ ID NO 22
<211> LENGTH: 10
```

```
<212> TYPE: PRT
<213> ORGANISM: Artificial Sequence
<220> FEATURE:
<223> OTHER INFORMATION: Description of Artificial Sequence:
      Myc-tag of pSM2NT vector

<400> SEQUENCE: 22

Glu Gln Lys Leu Ile Ser Glu Glu Asp Leu
1               5                   10

<210> SEQ ID NO 23
<211> LENGTH: 15
<212> TYPE: PRT
<213> ORGANISM: Artificial Sequence
<220> FEATURE:
<223> OTHER INFORMATION: Description of Artificial Sequence:
      immunogenic peptide

<400> SEQUENCE: 23

Arg Asn Lys Pro Val Ala Arg Gln Ala Pro Gly Lys Arg Lys Cys
1               5                   10                  15
```